United States Patent
McCall et al.

(10) Patent No.: US 7,183,386 B2
(45) Date of Patent: Feb. 27, 2007

(54) FELINE IMMUNOGLOBULIN E PROTEINS AND COMPOSITIONS THEREOF

(75) Inventors: Catherine McCall, Boulder, CO (US); Eric Weber, Fort Collins, CO (US)

(73) Assignee: Heska Corporation, Loveland, CO (US)

(*) Notice: Subject to any disclaimer, the term of this patent is extended or adjusted under 35 U.S.C. 154(b) by 451 days.

(21) Appl. No.: 10/409,772

(22) Filed: Apr. 7, 2003

(65) Prior Publication Data

US 2003/0216565 A1    Nov. 20, 2003

Related U.S. Application Data

(62) Division of application No. 09/479,614, filed on Jan. 7, 2000, now Pat. No. 6,573,372.

(60) Provisional application No. 60/115,033, filed on Jan. 7, 1999.

(51) Int. Cl.
*C07K 16/00* (2006.01)

(52) U.S. Cl. .............. 530/387.1; 530/388.22; 424/133.1; 424/141.1; 424/144.1; 424/185.1; 536/23.53

(58) Field of Classification Search .............. None
See application file for complete search history.

(56) References Cited

U.S. PATENT DOCUMENTS 5,965,709 A * 10/1999 Presta et al. ............. 530/387.3

OTHER PUBLICATIONS

Colman PM, Research in Immunology, 1994, 145:33-36.*
Gilbert et al., Veterinary Immunology and Immunopathology, 1998, 63:223-233.*

* cited by examiner

*Primary Examiner*—G. R. Ewoldt
*Assistant Examiner*—Michael Szperka
(74) *Attorney, Agent, or Firm*—Heska Corporation

(57) ABSTRACT

The invention relates to: nucleic acid molecules encoding the light chain and heavy chain of feline immunoglobulin E (IgE), including species-specific regions of feline IgE; proteins encoded by the nucleic acid molecules; inhibitors to the nucleic acids and proteins; antibodies to the proteins; cells transformed with the nucleic acid molecules; assays employing the transformed cells, nucleic acids, antibodies and/or proteins or portions thereof; methods for treating IgE-mediated responses (ie. allergy) using the materials provided; methods for eliciting an immune response to IgE and kits containing the nucleic acid molecules, proteins or derivatives thereof (ie. antibodies).

2 Claims, No Drawings

FELINE IMMUNOGLOBULIN E PROTEINS AND COMPOSITIONS THEREOF

CROSS REFERENCE TO RELATED APPLICATIONS

This application is a divisional of U.S. patent application Ser. No. 09/479,614, filed Jan. 7, 2000, now U.S. Pat. No. 6,573,372 B2, issued Jun. 3, 2003, entitled "FELINE IMMUNOGLOBULIN E MOLECULES AND COMPOSITIONS THEREOF"; which claims priority to U.S. Provisional Patent Application Serial No. 60/115,033, filed Jan. 7, 1999, entitled "FELINE IMMUNOGLOBULIN E MOLECULES AND RELATED METHODS"; all of which are incorporated by reference herein.

FIELD OF THE INVENTION

The present invention relates to the field of feline IgE-mediated responses, and materials and methods useful to alter natural process related to IgE-mediated responses. The present invention therefore relates to vaccine technology, small molecule/antibody technology, molecular biology tools, and immunological techniques related to feline IgE and its function.

BACKGROUND OF THE INVENTION

Allergic responses in mammals are known to be mediated by immunoglobulin E. IgE molecules bind the Fcε receptor on mast cells and, when complexed with antigen, trigger a cascade of events that leads to the release of allergic mediators (ie. histamine, prostaglandins and proteases). Thus, interference with the IgE/Fcε receptor interaction is an avenue for controlling allergic responses. Interference with the IgE antibody/Fcε receptor interaction will also affect the pathology of atopic disease, hyper IgE syndrome, internal parasite infections and B cell neoplasia.

The species-specific portion of the IgE, the IgE constant region (on the heavy chain and involved in Fcε receptor binding) is of particular importance in design and manufacture of compounds useful to interfere with the IgE/Fcε receptor interaction, because compounds which are specific for this region produce little interference with non-IgE/receptor interactions. Moreover, the IgE constant region can be utilized in the design and manufacture of vaccines useful to elicit species- and immunoglobulin-specific anti-IgE immune responses.

The DNA and amino acid sequences of IgE molecules from several species, including human, rat, mouse and dog, have been reported. Peptides derived from known IgE sequences have been used to generate antibodies which alter IgE function. U.S. Pat. No. 5,091,313 is directed to the prevention or control of IgE-mediated allergic symptoms through the use of monoclonal or polyclonal antibodies raised against epitopes present in B cell-associated or soluble human IgE. WO90/15878 discloses the use of peptides derived from human, rat or mouse IgE sequences to generate antibodies which inhibit IgE-mediated mast cell degranulation. U.S. Pat. No. 4,223,016 discloses the use of peptides derived from IgE sequences for allergic desensitization. U.S. Pat. No. 5,629,415 discloses the canine IgE sequence and uses therefor.

SUMMARY OF THE INVENTION

The present invention provides isolated nucleic acid molecules which encode a portion of the heavy chain of feline IgE, isolated proteins encoded by the nucleic acid molecules, recombinant constructs and cells comprising the nucleic acid compounds and/or proteins, antibodies to the isolated proteins, therapeutic compositions useful for treating feline IgE-mediated responses (including i.e., vaccines), methods for treating feline IgE-mediated responses, methods for eliciting a feline IgE-mediated immune response, and kits comprising the materials provided. The present invention also provides nucleic acid molecules, proteins and methods related to the feline IgE light chain.

The present invention therefore provides isolated nucleic acid molecules encoding a portion of a feline IgE heavy chain molecule, wherein said nucleic acid molecules comprise a nucleic acid sequence selected from the group consisting of:

(a) a nucleic acid sequence which has more than 82% identity to a nucleic acid sequence selected from the group consisting of: SEQ ID NO 1; and SEQ ID NO 28, wherein said identity can be determined using the DNAsis computer program and default parameters;

(b) a nucleic acid sequence which encodes a feline heavy chain protein which has more than 76% identity to an amino acid sequence selected from the group consisting of: SEQ ID NO 2; and SEQ ID NO 29, wherein said identity can be determined using the DNAsis computer program and default parameters;

(c) a nucleic acid sequence which encodes and a feline heavy chain protein encoded by an allelic variant of a nucleic acid sequence selected from the group consisting of: SEQ ID NO 1; and SEQ ID NO 28; and (d) a nucleic acid sequence which has more than 90% identity to a nucleic acid sequence selected from the group consisting of: SEQ ID NO 3; SEQ ID NO 4; SEQ ID NO 6; SEQ ID NO 7; SEQ ID NO 9; SEQ ID NO 10; SEQ ID NO 12; SEQ ID NO 13; SEQ ID NO 15; SEQ ID NO 16; SEQ ID NO 18; and SEQ ID NO 31; and (e) a nucleic acid molecule fully complementary to a nucleic acid molecule selected from the group consisting of: a nucleic acid molecule of (a); a nucleic acid molecule of (b); and a nucleic acid molecule of (c).

The preferred nucleic acid molecules are those with immunological significance. At the time of filing, nucleic acid molecules which encode those which encode the constant region, specifically those which encode a Fcε receptor (sometimes called "FcεR") binding region, is preferred. In particular, nucleic acid molecules which encode a feline IgE Fcε receptor binding region and which comprises SEQ ID NO 4, SEQ ID NO 7 or SEQ ID NO 10 are preferred. Also provided is a nucleic acid molecule which encodes a feline IgE constant region and comprises SEQ ID NO 13.

The present invention also provides nucleic acid molecules which encode a feline IgE light chain protein and which comprise a nucleic acid molecule which encodes a protein with more than 84% identity to SEQ ID NO 19, with a nucleic acid molecule which comprises SEQ ID NO 19 being preferred.

The present invention also comprises expression vectors and recombinant cells comprising the present nucleic acid molecules. Also provided are fusion protein constructs comprising the present nucleic acid compounds.

The present invention also comprises isolated proteins encoding a portion of a feline IgE heavy chain molecule, wherein said proteins comprise an amino acid sequence selected from the group consisting of:

(a) an amino acid sequence encoded by a nucleic acid sequence which has more than 82% identity to a nucleic acid sequence selected from the group consisting of: SEQ ID NO 1; and SEQ ID NO: 28, wherein said identity can be determined using the DNAsis computer program and default parameters;

(b) an amino acid sequence which has more than 76% identity to an amino acid sequence selected from the group consisting of: SEQ ID NO 2; and SEQ ID NO: 29, wherein said identity can be determined using the DNAsis computer program and default parameters;

(c) an amino acid sequence encoded by an allelic variant of a nucleic acid sequence selected from the group consisting of: SEQ ID NO 1; and SEQ ID NO: 28; and (d) an amino acid sequence encoded by a a nucleic acid sequence which has more than 90% identity to a nucleic acid sequence selected from the group consisting of: SEQ ID NO 3; SEQ ID NO 4; SEQ ID NO 6; SEQ ID NO 7; SEQ ID NO 9; SEQ ID NO 10; SEQ ID NO 12; SEQ ID NO 13; SEQ ID NO 15; SEQ ID NO 16; SEQ ID NO 18; SEQ ID NO 28; and SEQ ID NO 30.

The preferred embodiments of this aspect of the present invention include those proteins capable of binding to Fcε receptor, in particular, SEQ ID NO 5, SEQ ID NO 8, SEQ ID NO 11 and SEQ ID NO 14.

In another embodiment, there are provided antibodies selective for a protein of the present invention. In particular, antibodies designated H-100, H-101, H-102, H-103, H-106 are preferred.

In another embodiment, there are provided therapeutic compositions useful for inhibiting an immune response to feline IgE, wherein said therapeutic composition is selected from the group consisting of:

(a) a nucleic acid molecule of the present invention;
(b) a protein encoded by a nucleic acid of (a);
(c) an inhibitor of a nucleic acid of (a); and
(d) an inhibitor of a protein of (b).

Preferred embodiments of this aspect of the present invention are antibodies selective for the proteins of the present invention, in particular, H-100, H-101, H-102, H-103, H-106 are preferred.

Also provided by the present invention are methods to identify the ability of a test compound to interfere with IgE/Fcε interaction, comprising: contacting the test compound with a protein of the present invention; and determining whether the test compound and said protein interact.

Also provided by the present invention are methods for inhibiting an immune response to feline IgE, comprising administering at least one therapeutic composition of the present invention.

Also provided by the present invention are diagnostic kits, comprising a container comprising a at least one composition selected from the group consisting of:

(a) a nucleic acid molecule of the present invention;
(b) a protein encoded by a nucleic acid of (a);
(c) an inhibitor of a nucleic acid of (a); and
(d) an inhibitor of a protein of (b).

Also provided are isolated nucleic acid molecules encoding a portion of a feline IgE light chain protein, wherein said nucleic acid molecule comprises a nucleic acid sequence selected from the group consisting of:

(a) a nucleic acid sequence which has more than 84% identity to SEQ ID NO 19, and wherein said identity can be determined using the DNAsis computer program and default parameters;

(b) a nucleic acid sequence which encodes a feline heavy chain protein selected from the group consisting of: a feline heavy chain protein which has more than 61% identity to SEQ ID NO 20, wherein said identity can be determined using the DNAsis computer program and default parameters; and a feline heavy chain protein encoded by an allelic variant of SEQ ID NO 19;

(c) a nucleic acid sequence which has more than 95% identity to a nucleic acid sequence selected from the group consisting of: SEQ ID NO 23; and SEQ ID NO 25; and (d) a nucleic acid molecule fully complementary to a nucleic acid molecule selected from the group consisting of: a nucleic acid molecule of (a); a nucleic acid molecule of (b); and a nucleic acid molecule of (c).

Also provided are isolated proteins encoding a portion of a feline IgE light chain molecule, wherein said protein comprises an amino acid sequence selected from the group consisting of:

(a) an amino acid sequence encoded by a nucleic acid sequence which has more than 84% identity to SEQ ID NO 19, and wherein said identity can be determined using the DNAsis computer program and default parameters;

(b) an amino acid sequence which has more than 61% identity to SEQ ID NO 20, wherein said identity can be determined using the DNAsis computer program and default parameters;

(c) an amino acid sequence encoded by an allelic variant of SEQ ID NO 19; and (d) a nucleic acid sequence which has more than 95% identity to a nucleic acid sequence selected from the group consisting of: SEQ ID NO 23; and SEQ ID NO 25.

Definitions:

"Allelic variant" is meant to refer to a full length gene or partial sequence of a full length gene that occurs at essentially the same locus (or loci) as the referent sequence, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions).

"Antibody" as used herein includes both polyclonal and monoclonal antibodies as well as fragments thereof, such as Fv, Fab and F(ab)$_2$ fragments that are capable of binding antigen or hapten.

"Fcε receptor" means any Fcε receptor recognized in the art, including the "low" affinity or "high" affinity receptors, or any such new receptors discovered.

"Feline Fcε receptor binding region" means a region of the feline IgE molecule that is capable of binding to a Fcε receptor, including the entire, naturally-occurring binding region, portions thereof that bind to the Fcε receptor, or modifications of either the entire naturally-occurring binding region or portions thereof.

"Feline IgE-mediated immune response" means not only any humoral or cellular immune response, but also any biological response resulting from an IgE/Fcε receptor interaction.

"Fragment" is meant to refer to any subset of the referent nucleic acid molecule.

"Incite" means causing any affect, ie. stimulation, of the feline IgE-mediated immune response.

"Immunogenic amounts" means at least the minimal amount necessary to incite a feline IgE-mediated immune response.

"Proteins" means any compounds which comprise amino acids, including peptides, polypeptides, fusion proteins, etc.

Moreover, for the purposes of the present invention, the term "a" or "an" entity refers to one or more of that entity;

for example, "a protein" or "a nucleic acid molecule" refers to one or more of those compounds or at least one compound. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds. According to the present invention, an isolated, or biologically pure, protein or nucleic acid molecule is a compound that has been removed from its natural milieu. As such, "isolated" and "biologically pure" do not necessarily reflect the extent to which the compound has been purified. An isolated compound of the present invention can be obtained from its natural source, can be produced using molecular biology techniques or can be produced by chemical synthesis.

DETAILED DESCRIPTION OF THE INVENTION

The present invention provides isolated nucleic acid molecules which encode a portion of the heavy chain of feline IgE, isolated proteins encoded by the nucleic acid molecules, recombinant constructs and cells comprising the nucleic acid compounds and/or proteins, antibodies to the isolated proteins, inhibitors of the proteins and nucleic acids, therapeutic compositions useful for treating feline IgE-mediated responses (including i.e., vaccines), methods for treating feline IgE-mediated responses, methods for eliciting a feline IgE-mediated immune response, and kits comprising the materials provided. The present invention also provides feline IgE light chain nucleic- and amino acid molecules, and associated materials.

The present invention therefore provides isolated nucleic acid molecules encoding a portion of a feline heavy chain molecule, wherein said nucleic acid molecules have more than 82% identity to SEQ ID NO 1 and/or SEQ ID NO 28, and wherein said identity can be determined using the DNAsis computer program and default parameters, as well as nucleic acid molecules fully complementary to those nucleic acid molecules.

Moreover, there is provided isolated nucleic acid molecules encoding a portion of a feline IgE heavy chain molecule, wherein said nucleic acid molecule comprises a nucleic acid sequence selected from the group consisting of:

(a) a nucleic acid sequence which has more than 82% identity to a nucleic acid sequence selected from the group consisting of: SEQ ID NO 1; and SEQ ID NO 28, wherein said identity can be determined using the DNAsis computer program and default parameters;

(b) a nucleic acid sequence which encodes a feline heavy chain protein which has more than 76% identity to an amino acid sequence selected from the group consisting of: SEQ ID NO 2; and SEQ ID NO 29, wherein said identity can be determined using the DNAsis computer program and default parameters;

(c) a nucleic acid sequence which encodes and a feline heavy chain protein encoded by an allelic variant of a nucleic acid sequence selected from the group consisting of: SEQ ID NO 1; and SEQ ID NO 28; and (d) a nucleic acid sequence which has more than 90% identity to a nucleic acid sequence selected from the group consisting of: SEQ ID NO 3; SEQ ID NO 4; SEQ ID NO 6; SEQ ID NO 7; SEQ ID NO 9; SEQ ID NO 10; SEQ ID NO 12; SEQ ID NO 13; SEQ ID NO 15; SEQ ID NO 16; SEQ ID NO 18; and SEQ ID NO 31; and (e) a nucleic acid molecule fully complementary to a nucleic acid molecule selected from the group consisting of: a nucleic acid molecule of (a); a nucleic acid molecule of (b); and a nucleic acid molecule of (c).

Allelic variants, fragments and homologues are, by definition of "nucleic acid molecule", included within this and other embodiments.

The preferred nucleic acid molecules are those with immunologic significance. At the time of filing, nucleic acids which encode the constant region, specifically those nucleic acid molecules which encode the Fcε receptor binding region, are preferred. In particular, SEQ ID NO 4, SEQ ID NO 7, SEQ ID NO 10, and SEQ ID NO 13 and complements thereof are most preferred.

The present invention also provides nucleic acid molecules which encode a feline IgE light chain protein and which comprise a nucleic acid molecule which encodes a protein with more than 84% identity to SEQ ID NO 19, with a nucleic acid molecule which comprises SEQ ID NO 19 being preferred.

The present invention also comprises expression vectors and recombinant cells comprising the present nucleic acid molecules. Also provided are fusion proteins constructed using the present nucleic acid compounds.

Included within the scope of the present invention, with particular regard to the nucleic acids above, are allelic variants, degenerate sequences and homologues. Allelic variants are well known to those skilled in the art and would be expected to be found within a given cat since the genome is diploid and/or among a group of two or more cats. The present invention also includes variants due to laboratory manipulation, such as, but not limited to, variants produced during polymerase chain reaction amplification or site directed mutagenesis. It is also well known that there is a substantial amount of redundancy in the various codons which code for specific amino acids. Therefore, this invention is also directed to those nucleic acid sequences which contain alternative codons which code for the eventual translation of the identical amino acid. Also included within the scope of this invention are mutations either in the nucleic acid sequence or the translated protein which do not substantially alter the ultimate physical properties of the expressed protein. For example, substitution of valine for leucine, arginine for lysine, or asparagine for glutamine may not cause a change in functionality of the polypeptide. Lastly, a nucleic acid sequence homologous to the exemplified nucleic acid molecules (or allelic variants or degenerates thereof) will have at least 85%, preferably 90%, and most preferably 95% sequence identity with a nucleic acid molecule in the sequence listing.

Stringent hybridization conditions are determined based on defined physical properties of the gene to which the nucleic acid molecule is being hybridized, and can be defined mathematically. Stringent hybridization conditions are those experimental parameters that allow an individual skilled in the art to identify significant similarities between heterologous nucleic acid molecules. These conditions are well known to those skilled in the art. See, for example, Sambrook, et al., 1989, *Molecular Cloning: A Laboratory Manual*, Cold Spring Harbor Labs Press, and Meinkoth, et al., 1984, *Anal. Biochem.* 138, 267–284, each of which is incorporated by reference herein in its entirety. As explained in detail in the cited references, the determination of hybridization conditions involves the manipulation of a set of variables including the ionic strength (M, in moles/liter), the hybridization temperature (° C.), the concentration of nucleic acid helix destabilizing agents (such as formamide), the average length of the shortest hybrid duplex (n), and the percent G+C composition of the fragment to which an unknown nucleic acid molecule is being hybridized. For nucleic acid molecules of at least about 150 nucleotides, these variables are inserted into a standard mathematical formula to calculate the melting temperature, or $T_m$, of a given nucleic acid molecule. As defined in the formula below, $T_m$ is the temperature at which two complementary nucleic acid molecule strands will disassociate, assuming 100% complementarity between the two strands: $T_m$=81.5° C.+16.6 log M+0.41(% G+C)–500/n–0.61(% formamide). For nucleic acid molecules smaller than about 50 nucleotides, hybrid stability is defined by the dissociation temperature ($T_d$), which is defined as the temperature at which 50% of the duplexes dissociate. For these smaller molecules, the stability at a standard ionic strength is defined by the following equation: $T_d$=4(G+C)+2(A+T). A temperature of 5° C. below $T_d$ is used to detect hybridization between perfectly matched molecules.

Also well known to those skilled in the art is how base-pair mismatch, i.e. differences between two nucleic acid molecules being compared, including non-complementarity of bases at a given location, and gaps due to insertion or deletion of one or more bases at a given location on either of the nucleic acid molecules being compared, will affect $T_m$ or $T_d$ for nucleic acid molecules of different sizes. For example, $T_m$ decreases about 1° C. for each 1% of mismatched base-pairs for hybrids greater than about 150 bp, and $T_d$ decreases about 5° C. for each mismatched base-pair for hybrids below about 50 bp. Conditions for hybrids between about 50 and about 150 base-pairs can be determined empirically and without undue experimentation using standard laboratory procedures well known to those skilled in the art. These simple procedures allow one skilled in the art to set the hybridization conditions (by altering, for example, the salt concentration, the formamide concentration or the temperature) so that only nucleic acid hybrids with less than a specified % base-pair mismatch will hybridize. Stringent hybridization conditions are commonly understood by those skilled in the art to be those experimental conditions that will allow hybridization between molecules having about 30% or less base-pair mismatch (i.e., about 70% or greater identity). Because one skilled in the art can easily determine whether a given nucleic acid molecule to be tested is less than or greater than about 50 nucleotides, and can therefore choose the appropriate formula for determining hybridization conditions, he or she can determine whether the nucleic acid molecule will hybridize with a given gene under stringent hybridization conditions and similarly whether the nucleic acid molecule will hybridized under conditions designed to allow a desired amount of base pair mismatch.

Hybridization reactions are often carried out by attaching the nucleic acid molecule to be hybridized to a solid support such as a membrane, and then hybridizing with a labeled nucleic acid molecule, typically referred to as a probe, suspended in a hybridization solution. Examples of common hybridization reaction techniques include, but are not limited to, the well-known Southern and northern blotting procedures. Typically, the actual hybridization reaction is done under non-stringent conditions, i.e., at a lower temperature and/or a higher salt concentration, and then high stringency is achieved by washing the membrane in a solution with a higher temperature and/or lower salt concentration in order to achieve the desired stringency.

For example, if the skilled artisan wished to identify a nucleic acid molecule that hybridized under stringent hybridization conditions with a feline nucleic acid molecule of about 150 bp in length, the following conditions could preferably be used. The average G+C content of feline genome is about 53%. The unknown nucleic acid molecules would be attached to a support membrane, and the 150 bp probe would be labeled, e.g. with a radioactive tag. The hybridization reaction could be carried out in a solution comprising 2×SSC and 0% formamide, at a temperature of about 37° C. (low stringency conditions). Solutions of differing concentrations of SSC can be made by one of skill in the art by diluting a stock solution of 20×SSC (175.3 gram NaCl and about 88.2 gram sodium citrate in 1 liter of water, pH 7) to obtain the desired concentration of SSC. In order to achieve high stringency hybridization, the skilled artisan would calculate the washing conditions required to allow up to 30% base-pair mismatch. For example, in a wash solution comprising 1×SSC and 0% formamide, the $T_m$ of perfect hybrids would be about 86° C.:

$$81.5° C.+16.6 \log (0.15M)+(0.53\times 39)-(500/150)-(0.61\times 0)=86.3° C.$$

Thus, to achieve hybridization with nucleic acid molecules having about 30% base-pair mismatch, hybridization washes would be carried out at a temperature of about 56° C. It is thus within the skill of one in the art to calculate additional hybridization temperatures based on the desired percentage base-pair mismatch, formulae and G/C content disclosed herein. For example, it is appreciated by one skilled in the art that as the nucleic acid molecule to be tested for hybridization against nucleic acid molecules of the present invention having sequences specified herein becomes longer than 150 nucleotides, the $T_m$ for a hybridization reaction allowing up to 30% base-pair mismatch will not vary significantly from 56° C.

It is known in the art that there are commercially available computer programs for determining the degree of similarity between two nucleic acid sequences. These computer programs include various known methods to determine the percentage identity and the number and length of gaps between hybrid nucleic acid molecules. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, GCG™ (available from Genetics Computer Group, Madison, Wis.), DNAsis™ (available from Hitachi Software, San Bruno, Calif.) and MacVector™ (available from the Eastman Kodak Company, New Haven, Conn.). A preferred method to determine percent identity among amino acid sequences and also among nucleic acid sequences includes using the Compare function by maximum matching within the program DNAsis Version 2.1 using default parameters.

In one embodiment of the present invention, a preferred feline IgE nucleic acid molecule includes an isolated nucleic acid molecule which is at least about 50 nucleotides, or at least about 150 nucleotides, and which hybridizes under conditions which preferably allow about 50% base pair mismatch, more preferably under conditions which allow about 45% base pair mismatch, more preferably under conditions which allow about 40% base pair mismatch, more preferably under conditions which allow about 35% base pair mismatch, more preferably under conditions which allow about 30% base pair mismatch, more preferably under conditions which allow about 25% base pair mismatch, more preferably under conditions which allow about 20% base pair mismatch, more preferably under conditions which allow about 15% base pair mismatch, more preferably under conditions which allow about 10% base pair mismatch and even more preferably under conditions which allow about 5% base pair mismatch with a nucleic acid molecule selected from the group consisting of SEQ ID NO 1, SEQ ID NO 4, SEQ ID NO 7, SEQ ID NO 10, SEQ ID NO 13, SEQ ID NO 16, and/or SEQ ID NO 19.

Another embodiment of the present invention includes a nucleic acid molecule comprising at least about 150 basepairs, wherein the nucleic acid molecule hybridizes, in a solution comprising 1×SSC and 0% formamide, at a temperature of about 56° C., to a nucleic acid sequence selected from the group consisting of: SEQ ID NO 1; SEQ ID NO 3; SEQ ID NO 4; SEQ ID NO 6; SEQ ID NO 7; SEQ ID NO 9; SEQ ID NO 10; SEQ ID NO 12; SEQ ID NO 13; SEQ ID NO 15; SEQ ID NO 16; and SEQ ID NO 18. Also preferred are fragments of any of such nucleic acid molecules.

Comparison of nucleic acid sequence SEQ ID NO 1 (i.e., the nucleic acid sequence of a portion of the feline IgE heavy chain) with nucleic acid sequences reported in GenBank indicates that SEQ ID NO 1 showed the most homology, i.e. about 82% identity, between SEQ ID NO 1 and a *Canis familiaris* IgE heavy chain region (Accession Number L36872).

Additional preferred feline IgE nucleic acid molecules of the present invention include an isolated nucleic acid molecule which is at least about 50 nucleotides, or at least about 150 nucleotides, comprising a nucleic acid sequence that is preferably at least about 45% identical, more preferably about 50% identical, more preferably about 55% identical, more preferably about 60% identical, more preferably about 65% identical, more preferably about 70% identical, more preferably about 75% identical, more preferably about 80% identical, more preferably about 85% identical, more preferably about 90% identical and even more preferably about 95% identical to a nucleic acid sequence selected from the group consisting of SEQ ID NO 1, SEQ ID NO 4, SEQ ID NO 7, SEQ ID NO 10, SEQ ID NO 13, SEQ ID NO 16, and/or SEQ ID NO 19. Also preferred are fragments of any of such nucleic acid molecules. Percent identity may be determined using the Compare function by maximum matching within the program DNAsis Version 2.1 using default parameters.

Knowing the nucleic acid sequences of certain feline IgE nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain feline IgE nucleic acid molecules from other species. Such nucleic acid molecules can be obtained in a variety of ways including screening appropriate expression libraries with antibodies of the present invention; traditional cloning techniques using oligonucleotide probes of the present invention to screen appropriate libraries of DNA; and PCR amplification of appropriate libraries or DNA using oligonucleotide primers of the present invention. Preferred libraries to screen or from which to amplify nucleic acid molecules include canine cDNA libraries as well as genomic DNA libraries. Similarly, preferred DNA sources to screen or from which to amplify nucleic acid molecules include adult cDNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising feline IgE genes or other feline IgE nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. Minimal size characteristics are disclosed herein. The present invention includes oligonucleotides that can be used as, for example, probes to identify nucleic acid molecules, primers to produce nucleic acid molecules or therapeutic reagents to inhibit feline FcεRα protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

Recombinant molecules of the present invention may also (a) contain secretory signals (i.e., signal segment nucleic acid sequences) to enable an expressed feline IgE protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments, as well as natural signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Recombinant molecules may also include intervening and/or untranslated sequences surrounding and/or within the nucleic acid sequences of nucleic acid molecules of the present invention.

The following table summarizes the Sequence Listing, for convenience:

| Description of sequence | SEQ ID NO |
|---|---|
| DNA sequence which encodes a portion of a IgE heavy chain | 1 |
| AA sequence of a portion of a IgE heavy chain | 2 |
| reverse DNA complement to 1 | 3 |
| DNA sequence which encodes the most preferred FcεR binding region of the IgE heavy chain | 4 |
| AA sequence which is the most preferred FcεR binding region of the IgE heavy chain | 5 |
| reverse DNA complement to 3 | 6 |
| DNA sequence of more preferred FcεR binding region | 7 |
| AA sequence of 7 | 8 |
| reverse DNA complement to 7 | 9 |
| DNA sequence of preferred FcεR binding region | 10 |
| AA sequence of 10 | 11 |
| reverse DNA complement to 8 | 12 |
| DNA sequence of constant region | 13 |
| AA sequence of constant region | 14 |

-continued

| Description of sequence | SEQ ID NO |
|---|---|
| reverse DNA complement of 13 | 15 |
| DNA sequence of partial variable region | 16 |
| AA sequence of partial variable region | 17 |
| reverse DNA complement of 16 | 18 |
| DNA sequence which encodes the IgE light chain | 19 |
| AA sequence which is the IgE light chain | 20 |
| reverse DNA complement to 19 | 21 |
| DNA sequence of polyadenylation signal | 22 |
| DNA nucleotides 7–732 of SEQ ID NO:19 | 23 |
| reverse DNA complement of 23 (nuc 223–948 of SEQ ID NO:21) | 24 |
| DNA nucleotides 67–732 of SEQ ID NO:19 | 25 |
| AA 21–242 of SEQ ID NO:20 | 26 |
| DNA nucleotides 223–888 of SEQ ID NO:21 | 27 |
| DNA sequence which encodes a portion of a IgE heavy chain | 28 |
| AA sequence of a portion of a IgE heavy chain | 29 |
| reverse DNA complement to 28 | 30 |
| DNA nucleotides 1–1488 of 28 | 31 |
| Reverse complement of 31 | 32 |
| DNA nucleotides 1–1293 of SEQ ID NO:13 | 33 |
| Reverse complement of 33 (nuc 126–1418 of SEQ ID NO:15) | 34 |

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulation of feline IgE nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, insect, other animal, and plant cells. Preferred expression vectors of the present invention can direct gene expression in bacterial, yeast, insect and mammalian cells and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, insect and mammalian cells, such as, but not limited to, tac, lac, trp, trc, oxy-pro, omp/lpp, rrnB, bacteriophage lambda (such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, Pichia alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, *Rous sarcoma* virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with cats. The present invention also comprises expression vectors comprising a nucleic acid molecule described herein.

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Also provided by the present invention are recombinant cells transformed with a nucleic acid described herein. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing feline IgE proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), other insect, other animal and plant cells. Preferred host cells include bacterial, mycobacterial, yeast, parasite, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (normal dog kidney cell line for canine herpesvirus cultivation), CRFK cells (normal cat kidney cell line for feline herpesvirus cultivation), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi; Salmonella typhimurium*, including attenuated strains such as UK-1 $_x$3987 and SR-11 $_x$4072; *Spodoptera frugiperda; Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK$^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences. The phrase "operatively linked" refers to insertion of a nucleic acid molecule into an expression vector in a manner such that the molecule is able to be expressed when transformed into a host cell.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed, examples of which are disclosed herein.

A recombinant cell of the present invention includes any cell transformed with at least one of any nucleic acid molecule of the present invention. Suitable and preferred nucleic acid molecules as well as suitable and preferred recombinant molecules with which to transform cells are disclosed herein.

The present invention also provides isolated proteins encoding a portion of a feline IgE heavy chain molecule, wherein said proteins comprise an amino acid sequence selected from the group consisting of:

(a) an amino acid sequence encoded by a nucleic acid sequence which has more than 82% identity to a nucleic acid sequence selected from the group consisting of: SEQ ID NO 1; and SEQ ID NO: 28, wherein said identity can be determined using the DNAsis computer program and default parameters;

(b) an amino acid sequence which has more than 76% identity to an amino acid sequence selected from the group consisting of: SEQ ID NO 2; and SEQ ID NO: 29, wherein said identity can be determined using the DNAsis computer program and default parameters;

(c) an amino acid sequence encoded by an allelic variant of a nucleic acid sequence selected from the group consisting of: SEQ ID NO 1; and SEQ ID NO: 28; and (d) an amino acid sequence encoded by a a nucleic acid sequence which has more than 90% identity to a nucleic acid sequence selected from the group consisting of: SEQ ID NO 3; SEQ ID NO 4; SEQ ID NO 6; SEQ ID NO 7; SEQ ID NO 9; SEQ ID NO 10; SEQ ID NO 12; SEQ ID NO 13; SEQ ID NO 15; SEQ ID NO 16; SEQ ID NO 18; and SEQ ID NO 31.

Comparison of amino acid sequence SEQ ID NO 2 (i.e., the amino acid sequence of the heavy chain of feline IgE) with amino acid sequences reported in GenBank™ indicates that SEQ ID NO 2 showed the most homology, i.e., about 76% identity, with IgE protein of *Canis familiaris* (GenBank accession number 598109).

Also provided are isolated proteins encoding a portion of a feline IgE light chain molecule, wherein said protein comprises an amino acid sequence selected from the group consisting of:

(a) an amino acid sequence encoded by a nucleic acid sequence which has more than 84% identity to SEQ ID NO 19, and wherein said identity can be determined using the DNAsis computer program and default parameters;

(b) an amino acid sequence which has more than 61% identity to SEQ ID NO 20, wherein said identity can be determined using the DNAsis computer program and default parameters;

(c) an amino acid sequence encoded by an allelic variant of SEQ ID NO 19; and (d) a nucleic acid sequence which has more than 95% identity to a nucleic acid sequence selected from the group consisting of: SEQ ID NO 23; and SEQ ID NO 25. In another embodiment, there are provided isolated feline IgE light chain proteins, preferably, SEQ ID NO 19.

There are also provided recombinant cells comprising the proteins herein described.

According to the present invention, a feline IgE protein of the present invention refers to: a feline IgE protein; a feline IgE homolog; a feline IgE mimetope; a feline IgE substrate analog; or a feline IgE peptide. Preferably, a feline IgE molecule binds to Fcε receptors.

The present invention therefore provides proteins of the feline IgE. Both the light and heavy chains are provided, as are compositions comprising the two, as well as portions of either. In particular, isolated feline constant region proteins are preferred, although Fcε binding region proteins are most preferred. Proteins which would result from expression of the nucleic acid molecules herein disclosed are preferred, with the proteins which would result from expression of the exemplified compounds being most preferred. It is understood that proteins which would result from expression of allelic variants of the exemplified sequences, as well as proteins which would result from the expression of nucleic acid molecules which hybridize under stringent hybridization conditions to the nucleic acid molecules exemplified are within the scope of the present invention as well. Lastly, an amino acid sequence substantially homologous to a referent IgE protein will have at least 85% sequence identity, preferably 90%, and most preferably 95% sequence homology with the amino acid sequence of a referent IgE protein or a peptide thereof. For example, an amino acid sequence is substantially homologous to feline IgE protein if, when aligned with feline IgE protein, at least 85% of its amino acid residues are the same. SEQ ID NO 2 and SEQ ID NO 29 are the most preferred proteins.

In another embodiment, a preferred feline IgE protein includes a protein encoded by a nucleic acid molecule which is at least about 50 nucleotides, or about 150 nucleotides, and which hybridizes under conditions which preferably allow about 35% base pair mismatch, more preferably under conditions which allow about 30% base pair mismatch, more preferably under conditions which allow about 25% base pair mismatch, more preferably under conditions which allow about 20% base pair mismatch, more preferably under conditions which allow about 15% base pair mismatch, more preferably under conditions which allow about 10% base pair mismatch, and even more preferably under conditions which allow about 5% base pair mismatch with a nucleic acid molecule selected from the group consisting of: SEQ ID NO 2; SEQ ID NO 5; SEQ ID NO 8; SEQ ID NO 11; SEQ ID NO 14; and SEQ ID NO 17.

Another embodiment of the present invention includes a feline IgE protein encoded by a nucleic acid molecule selected from the group consisting of: a nucleic acid molecule comprising at least about 150 nucleotides, wherein said nucleic acid molecule comprising at least about 150 nucleotides hybridizes, in a solution comprising 1×SSC and 0% formamide, at a temperature of about 56° C., to a nucleic acid sequence selected from the group consisting of SEQ ID NO 1, SEQ ID NO 4, SEQ ID NO 7, SEQ ID NO 10, SEQ ID NO 13, SEQ ID NO 16, and/or SEQ ID NO 19; and a nucleic acid molecule comprising a fragment of any of said nucleic acid molecules comprising at least about 150 nucleotides.

Yet another preferred feline IgE protein of the present invention includes a protein encoded by a nucleic acid molecule which is preferably about 45% identical, more preferably about 50% identical, more preferably about 55% identical, more preferably about 60% identical, more preferably about 65% identical, more preferably about 70% identical, more preferably about 75% identical, more preferably about 80% identical, more preferably about 85% identical, more preferably about 90% identical and even more preferably about 95% identical to a nucleic acid molecule having the nucleic acid sequence SEQ ID NO 1, SEQ ID NO 4, SEQ ID NO 7, SEQ ID NO 10, SEQ ID NO 13, SEQ ID NO 16, and/or SEQ ID NO 19, and/or fragments of such proteins. Percent identity as used herein is determined using the Compare function by maximum matching within the program DNAsis Version 2.1 using default parameters.

More preferred feline IgE proteins of the present invention include proteins comprising amino acid sequences that are at least about 50%, preferably at least about 55%, more preferably at least about 60%, even more preferably at least about 65%, even more preferably at least about 70%, even more preferably at least about 75%, even more preferably at least about 80%, even more preferably at least about 85%, even more preferably at least about 90%, and even more preferably at least about 95%, identical to amino acid sequence SEQ ID NO 1, SEQ ID NO 4, SEQ ID NO 7, SEQ ID NO 10, SEQ ID NO 13, SEQ ID NO 16, and/or SEQ ID NO 19.

Preferred feline IgE proteins of the present invention include proteins that are at least about 50%, preferably at least about 55%, more preferably at least about 60%, even more preferably at least about 65%, even more preferably at least about 70%, even more preferably at least about 75%, even more preferably at least about 80%, even more preferably at least about 85%, even more preferably at least about 90%, and even more preferably at least about 95% identical to SEQ ID NO 2, SEQ ID NO 5, SEQ ID NO 7, SEQ ID NO 11, and/or SEQ ID NO 14.

A feline IgE heavy chain protein of the present invention, including a homolog, can be identified in a straight-forward manner by the protein's ability to bind to Fcε receptor. Examples of feline IgE protein homologs include feline IgE proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homolog is capable of binding to Fcε receptor.

Feline IgE protein homologs can be the result of natural allelic variation or natural mutation. Feline IgE protein homologs of the present invention can also be produced using techniques known in the art including, but not limited to, direct modifications to the protein or modifications to the gene encoding the protein using, for example, classic or recombinant nucleic acid techniques to effect random or targeted mutagenesis.

The minimal size of an IgE protein homolog of the present invention is a size sufficient to be encoded by a nucleic acid molecule capable of forming a stable hybrid (i.e., hybridize under stringent hybridization conditions) with the complementary sequence of a nucleic acid molecule encoding the corresponding natural protein. As such, the size of the nucleic acid molecule encoding such a protein homolog is dependent on nucleic acid composition and percent homology between the nucleic acid molecule and complementary sequence. It should also be noted that the extent of homology required to form a stable hybrid can vary depending on whether the homologous sequences are interspersed throughout the nucleic acid molecules or are clustered (i.e., localized) in distinct regions on the nucleic acid molecules. The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode a feline IgE protein homolog of the present invention is from about 12 to about 18 nucleotides in length. Thus, the minimal size of a feline IgE protein homolog of the present invention is from about 4 to about 6 amino acids in length. There is no limit, other than a practical limit, on the maximal size of such a nucleic acid molecule in that the nucleic acid molecule can include a portion of a gene, an entire gene, multiple genes, or portions thereof. The preferred size of a protein encoded by a nucleic acid molecule of the present invention depends on whether a full-length, fusion, multivalent, or functional portion of such a protein is desired. Preferably, the preferred size of a protein encoded by a nucleic acid molecule of the present invention is a portion of the protein that binds to IgE which is about 30 amino acids, more preferably about 35 amino acids and even more preferably about 44 amino acids in length.

As used herein, a feline refers to any member of the cat family, including domestic cats, wild cats and zoo cats. Examples of cats from which to isolate feline IgE proteins of the present invention (including isolation of the natural protein or production of the protein by recombinant or synthetic techniques) include, but are not limited to, domestic cats, lions, tigers, leopards, panthers, cougars, bobcats, lynx, jaguars, cheetahs, and servals, with domestic cats being more preferred and *Felis domesticus* cats being even more preferred.

The present invention also includes mimetopes of feline IgE proteins of the present invention. As used herein, a mimetope of a feline IgE protein of the present invention refers to any compound that is able to mimic the activity of such a feline IgE protein (e.g., ability to bind to Fcε receptors), often because the mimetope has a structure that mimics the feline IgE protein. It is to be noted, however, that the mimetope need not have a structure similar to a feline IgE protein as long as the mimetope functionally mimics the protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); synthetic or natural organic or inorganic molecules, including nucleic acids; and/or any other peptidomimetic compounds. Mimetopes of the present invention can be designed using computer-generated structures of feline IgE proteins of the present invention. Mimetopes can also be obtained by generating random samples of molecules, such as oligonucleotides, peptides or other organic molecules, and screening such samples by affinity chromatography techniques using the corresponding binding partner, (e.g., a feline Fcε receptor domain or anti-feline IgE antibody). A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modeling. The predicted mimetope structures can then be produced by, for example, chemical synthesis, recombinant DNA technology, or by isolating a mimetope from a natural source. Specific examples of feline IgE mimetopes include anti-idiotypic antibodies, oligonucleotides produced using Selex™ technology, peptides identified by random screening of peptide libraries and proteins identified by phage display technology. A preferred mimetope is a peptidomimetic compound that is structurally and/or functionally similar to a feline IgE protein of the present invention, particularly to the Fcε receptor-binding domain of the feline IgE protein.

One embodiment of a feline IgE protein of the present invention is a fusion protein that includes a feline IgE protein domain attached to one or more fusion segments. Suitable fusion segments for use with the present invention include, but are not limited to, segments that can: enhance a protein's stability; act as an immunopotentiator to enhance an immune response; act as an suppressor of immune response and/or assist purification of a feline IgE protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the feline IgE-containing domain of the protein and can be susceptible to cleavage in order to enable straight-forward recovery of a feline IgE protein. Fusion proteins are preferably produced by culturing a recombinant cell transformed with a fusion nucleic acid molecule that encodes a protein including the fusion segment attached to either the carboxyl and/or amino terminal end of a feline IgE-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); a "tag" domain (e.g., at least a portion of β-galactosidase, a strep tag peptide, other domains that can be purified using compounds that bind to the domain, such as monoclonal antibodies); and/or a linker and enzyme domain (e.g., alkaline phosphatase domain connected to a feline IgE protein by a linker). More preferred fusion segments include metal binding domains, such as a poly-histidine segment; a maltose binding domain; a strep tag peptide, such as that available from Biometra in Tampa, Fla.; and a phage T7 S10 peptide.

A feline IgE molecule of the present invention can also include chimeric molecules comprising a portion of a feline IgE molecule that binds to an Fcε receptor and a second molecule that enables the chimeric molecule to be bound to a substrate in such a manner that the IgE molecule portion binds to FcεR in essentially the same manner as an IgE molecule that is not bound to a substrate. An example of a suitable second molecule includes a portion of an immunoglobulin molecule or another ligand that has a suitable binding partner that can be immobilized on a substrate, e.g., biotin and avidin, or a metal-binding protein and a metal (e.g., His), or a sugar-binding protein and a sugar (e.g., maltose).

Chimeric immunoglobulin molecules are also included in the present invention. Specifically, a chimeric immunoglobulin molecule which contains a portion from a feline IgE and a portion that is not feline is contemplated. The non-feline portion is ideally the antigen binding site of the IgE, and therefore, should include less than about 1% non-feline sequence. A chimeric molecule ideally contains only those portions of the non-feline variable region that binds to antigen, with the remainder of the immunoglobulin comprising feline sequence.

A variety of procedures known in the art may be used to molecularly clone feline IgE DNA of the present invention. These methods include, but are not limited to, direct functional expression of the feline IgE genes following the construction of feline IgE-containing cDNA or genomic DNA library in an appropriate expression vector system. Another method is to screen feline IgE-containing cDNA or genomic DNA library constructed in a bacteriophage or plasmid shuttle vector with a labeled oligonucleotide probe designed from the amino acid sequence of the feline IgE subunits. An additional method consists of screening a feline IgE-containing cDNA or genomic DNA libraries constructed in a bacteriophage or plasmid shuttle vector with a partial DNA encoding the feline IgE. This partial DNA is obtained by the specific PCR amplification of feline IgE DNA fragments through the design of degenerate oligonucleotide primers from the amino acid sequence of the purified feline IgE.

The translation of the RNA into a peptide or a protein will result in the production of at least a portion of the feline IgE protein which can be identified, for example, by the activity of feline IgE protein or by immunological reactivity with an anti-feline IgE antibody. In this method, pools of mRNA isolated from feline IgE-producing cells can be analyzed for the presence of an RNA which encodes at least a portion of the feline IgE protein. Further fractionation of the RNA pool can be done to purify the feline IgE RNA from non-feline IgE RNA. The peptide or protein produced by this method may be analyzed to provide amino acid sequences which in turn are used to provide primers for production of feline IgE cDNA, or the RNA used for translation can be analyzed to provide nucleotide sequences encoding feline IgE and produce probes for the production of feline IgE cDNA. These methods are known in the art and can be found in, for example, Sambrook, J., Fritsch, E. F., Maniatis, T. in *Molecular Cloning: A Laboratory Manual, Second Edition*, Cold Spring Harbor Laboratory Press, Cold Spring Harbor, N.Y. 1989.

Other types of libraries, as well as libraries constructed from other cells or cell types, may be useful for isolating feline IgE-encoding DNA. Other types of libraries include, but are not limited to, cDNA libraries derived from other felines or cell lines derived from other felines, and genomic DNA libraries. Preparation of cDNA libraries can be performed by standard techniques. Well known cDNA library construction techniques can be found in, for example, Sambrook, J., et al., ibid.

DNA encoding feline IgE may also be isolated from a suitable genomic DNA library. Construction of genomic DNA libraries can be performed by standard techniques. Well known genomic DNA library construction techniques can be found in Sambrook, J., et al., ibid.

In order to clone the feline IgE gene by the above methods, knowledge of the amino acid sequence of feline IgE may be necessary. One may either use the sequences herein exemplified or purify feline IgE protein and sequence a portion of the protein by manual or automated sequencing. It is not necessary to determine the entire amino acid sequence, because the linear sequence of two regions of 6 to 8 amino acids from the protein can be determined and used to produce primers for PCR amplification of feline IgE DNA.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the feline IgE sequence but will be capable of hybridizing to feline IgE DNA even in the presence of DNA oligonucleotides with mismatches under appropriate conditions. Under alternate conditions, the mismatched DNA oligonucleotides may still sufficiently hybridize to the feline IgE DNA to permit identification and isolation of feline IgE encoding DNA.

In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a feline IgE protein of the present invention. Such a medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane. The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit few impurities.

In addition, recombinant feline IgE can be separated from other cellular proteins by use of an immunoaffinity column made with monoclonal or polyclonal antibodies specific for full length nascent feline IgE, or polypeptide fragments of feline IgE.

The present invention also includes isolated (i.e., removed from their natural milieu) antibodies that selectively bind to a feline IgE protein of the present invention or a mimetope thereof (i.e., anti-feline IgE antibodies). As used herein, the term "selectively binds to" a feline IgE protein refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid. An anti-feline IgE antibody preferably selectively binds to a feline IgE protein in such a way as to reduce the activity of that protein.

In particular, there are provided antibodies directed to the feline IgE. In particular, antibodies that bind specifically to the heavy and/or light chain of IgE are provided. Preferred are antibodies selective for the constant region of the feline IgE heavy chain, although more preferred are antibodies selective for the Fcε receptor-binding domain of the IgE heavy chain. In one preferred embodiment, there are provided antibodies selective for a protein selected from the group consisting of: SEQ ID NO 2; SEQ ID NO 5; SEQ ID NO 8; SEQ ID NO 11; SEQ ID NO 14; SEQ ID NO 17; SEQ ID NO 20; SEQ ID NO 26; and SEQ ID NO 29. These antibodies may be admixed or conjugated with additional materials, such as cytotic agents or other antibody fragments, including IgG fragments. In particular, antibodies as described in the examples are included, and preferred embodiments of the present invention, such as, H-100, H-101, H-102, H-103, H-106. However, those antibodies specific for the feline IgE light chain are also included, especially: H-99, H-104, and H-107.

Isolated antibodies of the present invention can include antibodies in a bodily fluid (such as, but not limited to, serum), or antibodies that have been purified to varying degrees. Antibodies of the present invention can be polyclonal or monoclonal. Functional equivalents of such antibodies, such as antibody fragments and genetically-engineered antibodies (including single chain antibodies or chimeric antibodies that can bind to more than one epitope) are also included in the present invention.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce feline IgE proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as tools to detect IgE in the presence or absence of Fcε receptor and/or (b) as tools to screen expression libraries and/or to recover desired proteins of the present invention from a mixture of proteins and other contaminants. Furthermore, antibodies of the present invention can be used to target cytotoxic agents to cells having Fcε receptors in order to directly kill such cells. Targeting can be accomplished by conjugating (i.e., stably joining) such antibodies to the cytotoxic agents using techniques known to those skilled in the art. Suitable cytotoxic agents are known to those skilled in the art. Antibodies of the present invention, including Fcε receptor binding site-binding portions thereof, can also be used, for example, to inhibit binding of IgE to Fcε receptors, to produce anti-feline IgE idiotypic antibodies, to purify cells having feline IgE proteins, to stimulate intracellular signal transduction through a feline Fcε and to identify cells having feline IgE proteins.

The above described methods for producing monospecific antibodies may be utilized to produce antibodies specific for feline IgE polypeptide fragments, or full-length nascent feline IgE polypeptide.

Polyclonal serum may be obtained by well-known methods, such as by immunizing an animal (ie. rabbit), with a feline IgE and isolating serum.

Another embodiment of the present invention are therapeutic compositions that, when administered to an animal in an effective manner, are capable of affecting IgE-mediated reactions associated with diseases related to biological responses involving IgE function. A therapeutic composition of the present invention can include: a nucleic acid of the present invention, a protein of the present invention or an inhibitor of the present invention.

By "inhibitor" it is meant that the compound inhibits the formation of a complex between feline IgE protein and Fcε receptor. Such inhibitors can, for example, interact with the feline Fcε receptor binding site on IgE, other regions on feline IgE that effect IgE binding to Fcε receptor or the IgE binding site, for example, by allosteric interaction, on Fcε receptor. An inhibitor of IgE and Fcε receptor complex formation protein can interfere with complex formation by, for example, preventing formation of an IgE protein and Fcε receptor complex or disrupting an existing IgE protein and Fcε receptor complex causing the IgE protein and Fcε receptor to dissociate. An inhibitor of IgE and Fcε receptor complex formation is usually a relatively small molecule. Preferably, an inhibitor of the present invention is derived from a feline IgE of the present invention, and more preferably from the Fcε receptor binding site of the IgE, and is identified by its ability to bind to, or otherwise interact with, a Fcε receptor protein, thereby interfering with the formation of a complex between a feline IgE protein and Fcε receptor.

Preferred inhibitors of a feline IgE protein of the present invention include, but are not limited to, feline IgE proteins, fragments or mimetopes thereof, a Fcε receptor binding analog of a feline IgE protein, and other molecules that bind to a feline IgE protein (e.g., to an allosteric site) or Fcε receptor in such a manner that Fcε receptor and IgE protein complex formation is inhibited. Preferred feline IgE proteins, fragments and mimetopes thereof are capable of binding to Fcε receptor in such a manner that feline IgE does not bind to Fcε receptor. Mimetopes include those disclosed herein.

A feline IgE protein binding analog refers to a compound that interacts with (e.g., binds to, associates with, modifies) the Fcε receptor-binding site of a feline IgE protein. A preferred feline IgE protein binding analog inhibits Fcε receptor-binding activity of a feline IgE protein. Feline IgE protein binding analogs can be of any inorganic or organic composition, and, as such, can be, but are not limited to, peptides, nucleic acids, and peptidomimetic compounds. Feline IgE protein substrate analogs can be, but need not be, structurally similar to a feline IgE protein's natural substrate (e.g., Fcε receptor) as long as they can interact with the active site (e.g., Fcε receptor-binding site of that feline IgE). Feline IgE protein binding analogs can be designed using computer-generated structures of feline IgE proteins of the present invention or computer structures of, for example, the IgE-binding domain of Fcε receptor. Binding analogs can also be obtained by generating random samples of molecules, such as oligonucleotides, peptides, peptidomimetic compounds, or other inorganic or organic molecules, and screening such samples by affinity chromatography techniques using the corresponding binding partner, (e.g., a feline IgE protein or anti-feline IgE idiotypic antibody). A preferred feline IgE protein binding analog is a peptidomimetic compound (i.e., a compound that is structurally and/or functionally similar to a natural feline Fcε receptor protein, particularly to the region of the substrate that binds to a feline IgE protein, but that inhibits IgE binding upon interacting with the Fcε receptor binding site).

Feline IgE molecules, as well as other inhibitors and therapeutic compounds, can be used directly as compounds in compositions of the present invention to treat animals as long as such compounds are not harmful to the animals being treated.

The present invention also includes a therapeutic composition comprising one or more therapeutic compounds of the present invention. Examples of such therapeutic compounds are disclosed herein.

A therapeutic composition of the present invention can be used to reduce an IgE-mediated biological response in an animal by administering such a composition to an animal. Preferably, an animal is treated by administering to the animal a therapeutic composition of the present invention in such a manner that a therapeutic compound (e.g., an inhibitor of a feline IgE protein, an anti-feline IgE antibody, an inhibitor of Fcε receptor, or nucleic acid molecules encoding feline IgE proteins) binds to an IgE molecule in the animal. Such administration could be by a variety of routes known to those skilled in the art including, but not limited to, subcutaneous, intradermal, intravenous, intranasal, oral, transdermal, intramuscular routes and other parenteral routes.

Compositions of the present invention can be administered to any animal having an IgE that binds to a therapeutic compound of the present invention or to a protein expressed by a nucleic acid molecule contained in a therapeutic composition. Preferred animals to treat include mammals and birds, with cats, dogs, horses, humans and other pets, work and/or economic food animals. Particularly preferred animals to protect are cats and dogs.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, cresols, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), granulocyte colony stimulating factor (G-CSF), macrophage colony stimulating factor (M-CSF), colony stimulating factor (CSF), Flt-3 ligand, erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation, normal T cell expressed and presumably secreted), macrophage inflammatory proteins (e.g., MIP-1 alpha and MIP-1 beta), and Leishmania elongation initiating factor (LEIF); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposopheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of an animal at a constant rate sufficient to attain therapeutic dose levels of the composition to reduce Fcε receptor-mediated biological responses in the animal. As used herein, Fcε receptor-mediated biological response refers to cellular responses that occur when IgE is complexed with Fcε receptor. For example, a Fcε-mediated biological response includes release of biological mediators, such as histamine, prostaglandins and/or proteases, that can trigger clinical symptoms of allergy. The therapeutic composition is preferably released over a period of time ranging from about 1 to about 12 months. A preferred controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

Acceptable protocols to administer therapeutic compositions of the present invention in an effective manner include individual dose size, number of doses, frequency of dose administration, and mode of administration. Determination of such protocols can be accomplished by those skilled in the art. A suitable single dose is a dose that is capable of protecting (i.e., preventing or treating) an animal from disease when administered one or more times over a suitable time period. The need for additional administrations of a therapeutic composition can be determined by one of skill in the art in accordance with the given condition of a patient. For example, to regulate an antigen-specific Fcε receptor-mediated response, a therapeutic composition may be administered more frequently when an antigen is present in a patient's environment in high amounts and less frequently when the antigen is present in lower amounts.

According to one embodiment, a nucleic acid molecule of the present invention can be administered to an animal in a fashion to enable expression of that nucleic acid molecule into a feline IgE protein or a feline IgE RNA (e.g., antisense RNA, ribozyme, triple helix forms or RNA drug) in the animal. Nucleic acid molecules can be delivered to an animal in a variety of methods including, but not limited to, (a) administering a naked (i.e., not packaged in a viral coat or cellular membrane) nucleic acid molecule (e.g., as naked DNA or RNA molecules, such as is taught, for example in Wolff et al., 1990, *Science* 247, 1465–1468) or (b) administering a nucleic acid molecule packaged as a recombinant virus or as a recombinant cell (i.e., the nucleic acid molecule is delivered by a viral or cellular vehicle).

A naked nucleic acid molecule of the present invention includes a nucleic acid molecule of the present invention and preferably includes a recombinant molecule of the present invention that preferably is replication, or otherwise amplification, competent. A naked nucleic acid of the present invention can comprise one or more nucleic acid molecules of the present invention in the form of, for example, a bicistronic recombinant molecule having, for example one or more internal ribosome entry sites. Preferred naked nucleic acid molecules include at least a portion of a viral genome (i.e., a viral vector). Preferred viral vectors include those based on alphaviruses, poxviruses, adenoviruses, herpesviruses, picornaviruses, and retroviruses, with those based on alphaviruses (such as Sindbis or Semliki virus), species-specific herpesviruses and species-specific poxviruses being particularly preferred. Any suitable transcription control sequence can be used, including those disclosed as suitable for protein production. Particularly preferred transcription control sequence include cytomegalovirus intermediate early (preferably in conjunction with Intron-A), Rous Sarcoma Virus long terminal repeat, and tissue-specific transcription control sequences, as well as transcription control sequences endogenous to viral vectors if viral vectors are used. The incorporation of "strong" poly(A) sequences are also preferred.

Naked nucleic acid molecules of the present invention can be administered by a variety of methods. Suitable delivery methods include, for example, intramuscular injection, subcutaneous injection, intradermal injection, intradermal scarification, particle bombardment, oral application, and nasal application, with intramuscular injection, intradermal injection, intradermal scarification and particle bombardment being preferred. A preferred single dose of a naked DNA molecule ranges from about 1 nanogram (ng) to about 1 milligram (mg), depending on the route of administration and/or method of delivery, as can be determined by those skilled in the art. Examples of administration methods are disclosed, for example, in U.S. Pat. No. 5,204,253, by Bruner, et al., issued Apr. 20, 1993, PCT Publication No. WO 95/19799, published Jul. 27, 1995, by McCabe, and PCT Publication No. WO 95/05853, published Mar. 2, 1995, by Carson, et al. Naked DNA molecules of the present invention can be contained in an aqueous excipient (e.g., phosphate buffered saline) and/or with a carrier (e.g., lipid-based vehicles), or it can be bound to microparticles (e.g., gold particles).

A recombinant virus of the present invention includes a recombinant molecule of the present invention that is packaged in a viral coat and that can be expressed in an animal after administration. Preferably, the recombinant molecule is packaging-deficient and/or encodes an attenuated virus. A number of recombinant viruses can be used, including, but not limited to, those based on alphaviruses, poxviruses, adenoviruses, herpesviruses, picornaviruses and retroviruses. Preferred recombinant viruses are those based on alphaviruses (such as Sindbis virus), raccoon poxviruses, species-specific herpesviruses and species-specific poxviruses. An example of methods to produce and use alphavirus recombinant virus is disclosed in PCT Publication No. WO 94/17813, by Xiong et al., published Aug. 18, 1994, which is incorporated by reference herein in its entirety.

When administered to an animal, a recombinant virus of the present invention infects cells within the recipient animal and directs the production of a protein or RNA nucleic acid molecule that is capable of reducing Fcε receptor-mediated biological responses in the animal. For example, a recombinant virus comprising a feline IgE nucleic acid molecule of the present invention is administered according to a protocol that results in the animal producing an amount of protein or RNA sufficient to reduce IgE-mediated biological responses. A preferred single dose of a recombinant virus of the present invention is from about $1\times10^4$ to about $1\times10^7$ virus plaque forming units (pfu) per kilogram body weight of the animal. Administration protocols are similar to those described herein for protein-based compositions, with subcutaneous, intramuscular, intranasal and oral administration routes being preferred.

A recombinant cell useful in a therapeutic composition of the present invention includes recombinant cells of the present invention that comprises at least one feline IgE of the present invention. Preferred recombinant cells for this embodiment include Salmonella, E. coli, Listeria, Mycobacterium, S. frugiperda, yeast, (including Saccharomyces cerevisiae), BHK, CV-1, myoblast G8, COS (e.g., COS-7), Vero, MDCK and CRFK recombinant cells. A recombinant cell of the present invention can be administered in a variety of ways but have the advantage that they can be administered orally, preferably at doses ranging from about $10^8$ to about $10^{12}$ cells per kilogram body weight. Administration protocols are similar to those described herein for protein compositions. Recombinant cells can comprise whole cells, cells stripped of cell walls or cell lysates. Pharmaceutically useful compositions comprising feline IgE DNA, feline IgE RNA, or feline IgE protein, or other modulators of feline IgE activity, such as mimetopes, analogs, homologs, chimeras which inhibit the IgE/Fcε receptor interaction, may be formulated according to known methods such as by the admixture of a pharmaceutically acceptable carrier, or by modification with additional chemical moieties so as to form a chemical derivative. Examples of such carriers, modifications and methods of formulation may be found in Remington's Pharmaceutical Sciences. To form a pharmaceutically acceptable composition suitable for effective administration, such compositions will contain an effective amount of the protein, DNA, RNA, or modulator.

The present invention also has the objective of providing suitable topical, oral, systemic and parenteral formulations of the pharmaceutical compounds herein provided. The formulations can be administered in a wide variety of therapeutic dosage forms in conventional vehicles for administration. For example, the compounds can be formulated for oral administration in the form of tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a feline IgE modulating agent.

In addition, a feline IgE molecule formulation of the present invention can include not only a feline IgE molecule but also one or more additional antigens or antibodies useful to affect immunogenic change in an animal. As used herein, an antigen refers to any molecule capable of being selectively bound by an antibody. As used herein, selective binding of a first molecule to a second molecule refers to the ability of the first molecule to preferentially bind (e.g., having higher affinity higher avidity) to the second molecule when compared to the ability of a first molecule to bind to a third molecule. The first molecule need not necessarily be the natural ligand of the second molecule. Examples of such antibodies include, but are not limited to, antibodies that bind selectively to the constant region of an IgE heavy (i.e., anti-IgE isotype antibody) or antibodies that bind selectively to an IgE having a specific antigen specificity (i.e., anti-IgE idiotypic antibody). Suitable anti-IgE antibodies for use in a formulation of the present invention are not capable of cross-linking two or more IgE antibodies. Preferred anti-IgE antibodies include Fab fragments of the antibodies (as defined in Janeway et al., ibid.). Examples of such antigens include any antigen known to induce immunogenic change in an animal. Preferred antigens include allergens and parasite antigens. Allergens of the present invention are preferably derived from fungi, trees, weeds, shrubs, grasses, wheat, corn, soybeans, rice, eggs, milk, cheese, bovines (or cattle), poultry, swine, cats, sheep, yeast, fleas, flies, mosquitos, mites, midges, biting gnats, lice, bees, wasps, ants, true bugs or ticks. A suitable flea allergen includes an allergen derived from a flea, in particular flea saliva antigen. A preferred flea allergen includes a flea saliva antigen. Preferred flea saliva antigens include antigens such as those disclosed in PCT Patent Publication No. WO 96/11271, published Apr. 18, 1996, by Frank et al. (this publication is incorporated by reference herein in its entirety), with flea saliva products and flea saliva proteins being particularly preferred. According to the present invention, a flea saliva protein includes a protein produced by recombinant DNA methods, as well as proteins isolated by other methods disclosed in PCT Patent Publication No. WO 96/11271.

Preferred general allergens include those derived from grass, Meadow Fescue, curly dock, plantain, Mexican firebush, lamb's quarters, pigweed, ragweed, sage, elm, cocklebur, box elder, walnut, cottonwood, ash, birch, cedar, oak, mulberry, cockroach, *Dermataphagoides, Alternaria, Aspergillus, Cladosporium, Fusarium, Helminthosporium, Mucor, Penicillium, Pullularia, Rhizopus* and/or *Tricophyton*. More preferred general allergens include those derived from Johnson grass, Kentucky blue grass, meadow fescue, orchard grass, perennial rye grass, red top grass, timothy grass, Bermuda grass, brome grass, curly dock, English plantain, Mexican firebush, lamb's quarters, rough pigweed short ragweed, wormwood sage, American elm, common cocklebur, box elder, black walnut, eastern cottonwood, green ash, river birch, red cedar, red oak, red mulberry, cockroach, *Dermataphagoides farinae, Alternaria alternata, Aspergillus fumigatus, Cladosporium herbarum, Fusarium vasinfectum, Helminthosporium sativum, Mucor recemosus, Penicillium notatum, Pullularia pullulans, Rhizopus nigricans* and/or Tricophyton spp. Preferred parasite antigens include, but are not limited to, helminth antigens, in particular heartworm antigens, such as Di33 (described in U.S. patent application Ser. No. 08/715,628, filed Sep. 18, 1996, by Grieve et al., which is incorporated by reference herein in its entirety). The term "derived from" refers to a natural allergen of such plants or organisms (i.e., an allergen directly isolated from such plants or organisms), as well as, non-natural allergens of such plants or organisms that posses at least one epitope capable of eliciting an immune response against an allergen (e.g., produced using recombinant DNA technology or by chemical synthesis).

A feline IgE molecule can be combined with a buffer in which the feline IgE molecule is solubilized, and/or with a carrier. Suitable buffers and carriers are known to those skilled in the art. Examples of suitable buffers include any buffer in which a feline IgE molecule can function to selectively bind to IgE, such as, but not limited to, phosphate buffered saline, water, saline, phosphate buffer, bicarbonate buffer, HEPES buffer (N-2-hydroxyethylpiperazine-N'-2-ethanesulfonic acid buffered saline), TES buffer (Tris-EDTA buffered saline), Tris buffer and TAE buffer (Tris-acetate-EDTA). Examples of carriers include, but are not limited to, polymeric matrices, toxoids, and serum albumins, such as bovine serum albumin. Carriers can be mixed with feline IgE molecules or conjugated (i.e., attached) to feline IgE molecules in such a manner as to not substantially interfere with the ability of the feline IgE molecules to selectively bind to Fcε receptor.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water, and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride, and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methylcellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations. The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacryl-amidephenol, polyhydroxy-ethylaspartamidephenol, or polyethyleneoxidepolyl-ysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

In another embodiment of the present invention, there are provided methods to inhibit or elicit an IgE-mediated immune response, comprising administering a therapeutic compound of the present invention.

One embodiment of the present invention is a method of immunotherapy comprising the steps of: (a) administering to an animal an effective amount of a therapeutic composition of an inhibitor of feline IgE and Fcε receptor complex formation. Suitable therapeutic compositions and methods of administration methods are disclosed herein. According to the present invention, a therapeutic composition and method of the present invention can be used to prevent or alleviate symptoms associated with IgE-mediated biological responses.

The efficacy of a therapeutic composition of the present invention to effect IgE-mediated biological responses can be tested using standard methods for detecting IgE-mediated immunity including, but not limited to, immediate hypersensitivity, delayed hypersensitivity, antibody-dependent cellular cytotoxicity (ADCC), immune complex activity, mitogenic activity, histamine release assays and other methods such as those described in Janeway et al., ibid.

The present invention also provides methods to identify the ability of a test compound to interfere with IgE/Fcε receptor interaction, comprising: contacting the test compound with a protein of the present invention; and determining whether the test compound and said protein interact.

In particular, there are provided methods to identify the ability of a test compound to interfere with IgE/Fcε receptor interaction comprising: (a) contacting an isolated feline IgE molecule with a test compound/Fcε receptor containing solution under conditions suitable for formation of an IgE molecule:Fcε receptor complex; and (b) determining the ability of the test compound to interfere with IgE/Fcε interaction by detecting the IgE molecule:Fcε receptor complex, the presence of the IgE molecule:Fcε receptor complex indicating the presence of IgE. A preferred feline IgE molecule is one which a carbohydrate group of the feline IgE molecule is conjugated to biotin.

Another embodiment of the present invention is a method to identify the ability of a test compound to interfere with IgE/Fcε interaction comprising: (a) contacting a Fcε receptor-bearing cell test compound and an IgE molecule of the present invention under conditions suitable for formation of a recombinant cell:IgE complex; and (b) determining the ability of the test compound to interfere with IgE/Fcε receptor interaction by detecting the recombinant cell:IgE complex, the presence of the recombinant cell:IgE complex indicating the ability of the test compound to interfere with IgE/Fcε receptor interaction.

A preferred method to detect the ability of the test compound to interfere with IgE/Fcε receptor interaction comprises: (a) immobilizing a presently-disclosed IgE or a Fcε receptor molecule on a substrate; (b) contacting the IgE or Fcε receptor molecule with the test compound under conditions suitable for formation of an IgE molecule:Fcε receptor complex bound to the substrate; (c) removing non-bound material from the substrate under conditions that retain Fcε receptor molecule:IgE complex binding to the substrate; and (d) detecting the presence of the IgE molecule:Fcε receptor complex.

Also included are methods to detect IgE, which comprise: (a) immobilizing a test compound on a substrate; (b) contacting the test compound with a presently-disclosed feline IgE molecule under conditions suitable for formation of a feline IgE molecule:test compound complex bound to the substrate; (c) removing non-bound material from the substrate under conditions that retain feline IgE molecule:test compound complex binding to the substrate; and (d) detecting the presence of the feline IgE molecule:test compound complex.

A preferred method to detect IgE comprises: (a) immobilizing Fcε receptor on a substrate; (b) contacting a test compound with a presently-disclosed feline IgE molecule under conditions suitable for formation of a IgE:test compound complex bound to the Fcε receptor on the substrate; (c) removing non-bound material from the Fcε receptor on the substrate under conditions that retain feline IgE molecule:test compound complex binding to the Fcε receptor on the substrate; and (d) detecting the presence of the feline IgE molecule:test compound complex.

One embodiment of the present invention is a method to detect IgE nucleic acid which includes the steps of: (a) contacting an isolated feline IgE nucleic acid molecule with a putative IgE nucleic acid-containing composition under conditions suitable for formation of a feline IgE nucleic acid molecule:IgE nucleic acid complex; and (b) detecting the presence of IgE nucleic acid by detecting the feline IgE nucleic acid molecule:IgE nucleic acid complex. Presence of such a feline IgE nucleic acid molecule:IgE nucleic acid complex indicates that the animal is producing IgE. Preferred IgE to detect using a feline IgE nucleic acid molecule include feline IgE, canine IgE, equine IgE and human IgE, with feline IgE being particularly preferred.

As used herein, canine refers to any member of the dog family, including domestic dogs, wild dogs and zoo dogs. Examples of dogs include, but are not limited to, domestic dogs, wild dogs, foxes, wolves, jackals and coyotes. As used herein, equine refers to any member of the horse family, including horses, donkeys, mules and zebras.

As used herein, the term "contacting" refers to combining or mixing ingredients, as all of those terms are known in the art. "Formation of a complex" refers to the ability of the molecules to form a stable complex that can be measured (i.e., detected). Binding between a feline Fcε receptor and a feline IgE molecule is effected under conditions suitable to form a complex; such conditions (e.g., appropriate concentrations, buffers, temperatures, reaction times) as well as methods to optimize such conditions are known to those skilled in the art, and examples are disclosed herein. Examples of complex formation conditions are also disclosed in, for example, in Sambrook et al., ibid.

As used herein, the term "detecting complex formation" refers to determining if any complex is formed, i.e., assaying for the presence (i.e., existence) of a complex. If complexes are formed, the amount of complexes formed can, but need not be, determined. Complex formation, or selective binding, e.g., between Fcε receptor and feline IgE molecules in the composition can be measured (i.e., detected, determined) using a variety of methods standard in the art (see, for example, Sambrook et al. ibid.), examples of which are disclosed herein.

In one embodiment, a test compound of the present method includes a biological sample from an animal. A suitable biological sample includes, but is not limited to, a bodily fluid composition or a cellular composition. A bodily fluid refers to any fluid that can be collected (i.e., obtained) from an animal, examples of which include, but are not limited to, blood, serum, plasma, urine, tears, aqueous humor, cerebrospinal fluid (CSF), saliva, lymph, nasal secretions, milk and feces. Such a composition of the present method can, but need not be, pretreated to remove at least some of the non-IgE isotypes of immunoglobulin and/or other proteins, such as albumin, present in the fluid. Such removal can include, but is not limited to, contacting the bodily fluid with a material, such as Protein G, to remove IgG antibodies and/or affinity purifying IgE antibodies from other components of the body fluid by exposing the fluid to, for example, Concanavalin A. In another embodiment, a composition includes collected bodily fluid that is pretreated to concentrate immunoglobulin contained in the fluid. For example, immunoglobulin contained in a bodily fluid can be precipitated from other proteins using ammonium sulfate. A preferred composition of the present method is serum.

A complex can be detected in a variety of ways including, but not limited to use of one or more of the following assays- an enzyme-linked immunoassay, a radioimmunoassay, a fluorescence immunoassay, a chemiluminescent assay, a lateral flow assay, an agglutination assay, a particulate-based assay (e.g., using particulates such as, but not limited to, magnetic particles or plastic polymers, such as latex or polystyrene beads), an immunoprecipitation assay, a Bio-Core™ assay (e.g., using colloidal gold) and an immunoblotting assay (e.g., a western blot). Another preferred method is a flow-through assay, examples of which are disclosed in U.S. Pat. No. 4,727,019, issued Feb. 23, 1988, by Valkirs et al, which is incorporated by reference in its entirety. Such assays are well known to those skilled in the art. Assays can be used to give qualitative or quantitative results depending on how they are used. Some assays, such as agglutination, particulate separation, and immunoprecipitation, can be observed visually (e.g., either by eye or by a machines, such as a densitometer or spectrophotometer) without the need for a detectable marker. In other assays, conjugation (i.e., attachment) of a detectable marker to the feline IgE molecule or to a reagent that selectively binds to the feline IgE protein or nucleic acid or to the molecule being detected (described in more detail below) aids in detecting complex formation. Examples of detectable markers include, but are not limited to, a radioactive label, an enzyme, a fluorescent label, a chemiluminescent label, a chromophoric label or a ligand. A ligand refers to a molecule that binds selectively to another molecule. Preferred detectable markers include, but are not limited to, fluorescein, a radioisotope, a phosphatase (e.g., alkaline phosphatase), biotin, avidin, a peroxidase (e.g., horseradish peroxidase) and biotin-related compounds or avidin-related compounds (e.g., streptavidin or ImmunoPure® NeutrAvidin available from Pierce, Rockford, Ill.). According to the present invention, a detectable marker can be connected to a feline IgE molecule using, for example, chemical conjugation or recombinant DNA technology (e.g., connection of a fusion segment such as that described herein for a metal binding domain; an immunoglobulin binding; a sugar binding domain; and a "tag" domain). Preferably a carbohydrate group of the feline IgE molecule is chemically conjugated to biotin.

In one embodiment, a complex is detected by contacting a test compound with a feline IgE that is conjugated to a detectable marker. A suitable detectable marker to conjugate to a feline IgE molecule includes, but is not limited to, a radioactive label, a fluorescent label, an enzyme label, a chemiluminescent label, a chromophoric label or a ligand. A detectable marker is conjugated to a feline IgE molecule in such a manner as not to block the ability of the feline IgE molecule to bind to the compound being detected. Preferably, a feline IgE molecule is conjugated to biotin.

In one preferred embodiment, a feline IgE molecule:test compound complex is detected by contacting the complex with an indicator molecule that selectively binds to a feline IgE molecule of the present invention. Examples of such indicator molecule includes, but are not limited to, an antibody that selectively binds to a feline IgE molecule (referred to herein as an anti-feline IgE antibody) or a compound that selectively binds to a detectable marker conjugated to a feline IgE molecule, such as human Fcε receptor, Feline Fcε receptor, or an antigen that binds to an IgE. A feline IgE molecule conjugated to biotin is preferably detected using streptavidin, more preferably using ImmunoPure® NeutrAvidin (available from Pierce, Rockford, Ill.).

In another preferred embodiment, a feline IgE molecule: test compound complex is detected by contacting the complex with indicator molecule that selectively binds to an anti-test compound antibody. As used herein, an anti-test compound antibody includes not only a complete antibody but also any subunit or portion thereof that is capable of selectively binding to test compound. For example, an anti-test compound antibody can include an Fab fragment or a $F(ab')_2$ fragment, both of which are described in detail in Janeway et al., in *Immunobiology, the Immune System in Health and Disease*, Garland Publishing, Inc., NY, 1996 (which is incorporated herein by this reference in its entirety).

In one embodiment a complex can be formed and detected in solution. In another embodiment, a complex can be formed in which one or more members of the complex are immobilized on (e.g., coated onto) a substrate. Immobilization techniques are known to those skilled in the art. Suitable substrate materials include, but are not limited to, plastic, glass, gel, celluloid, paper, PVDF (poly-vinylidene-fluoride), nylon, nitrocellulose, and particulate materials such as latex, polystyrene, nylon, nitrocellulose, agarose and magnetic resin. Suitable shapes for substrate material include, but are not limited to, a well (e.g., microtiter dish well), a plate, a dipstick, a bead, a lateral flow apparatus, a membrane, a filter, a tube, a dish, a celluloid-type matrix, a magnetic particle, and other particulates. A particularly preferred substrate comprises an ELISA plate, a dipstick, a radioimmunoassay plate, agarose beads, plastic beads, latex beads, immunoblot membranes and immunoblot papers. In one embodiment, a substrate, such as a particulate, can include a detectable marker. Another preferred method is a flow-through assay, examples of which are disclosed in U.S. Pat. No. 4,727,019, issued Feb. 23, 1988, by Valkirs et al, which is incorporated by reference in its entirety.

A preferred method to detect feline IgE molecules of the present invention is an immunosorbent assay. An immunoabsorbent assay of the present invention comprises a capture molecule and an indicator molecule. A capture molecule of the present invention binds to an IgE in such a manner that the IgE is immobilized to a substrate. As such, a capture molecule is preferably immobilized to a substrate of the present invention prior to exposure of the capture molecule to a putative IgE-containing composition. An indicator molecule of the present invention detects the presence of an IgE bound to a capture molecule. As such, an indicator molecule preferably is not immobilized to the same substrate as a capture molecule prior to exposure of the capture molecule to a putative IgE-containing composition.

A preferred immunoabsorbent assay method includes a step of either: (a) immobilizing a feline IgE molecule on a substrate prior to contacting a feline IgE molecule with a test compound to form a feline IgE molecule-immobilized substrate; and (b) binding a test compound on a substrate prior to contacting a feline IgE molecule with a test compound to form a test compound-bound substrate. Preferably, the substrate includes a non-coated substrate, a feline IgE molecule-immobilized substrate, an antigen-immobilized substrate or an anti-IgE antibody-immobilized substrate.

Both a capture molecule and an indicator molecule of the present invention are capable of binding to an IgE. Preferably, a capture molecule binds to a different region of an IgE than an indicator molecule, thereby allowing a capture molecule to be bound to an IgE at the same time as an indicator molecule. The use of a reagent as a capture molecule or an indicator molecule depends upon whether the molecule is immobilized to a substrate when the molecule is exposed to an IgE. For example, a feline IgE molecule of the present invention is used as a capture molecule when the feline IgE molecule is bound on a substrate. Alternatively, a feline IgE molecule is used as an indicator molecule when the feline IgE molecule is not bound on a substrate. Suitable molecules for use as capture molecules or indicator molecules include, but are not limited to, a feline IgE molecule of the present invention, an antigen reagent or an anti-IgE antibody reagent of the present invention.

An immunoabsorbent assay of the present invention can further comprise one or more layers and/or types of secondary molecules or other binding molecules capable of detecting the presence of an indicator molecule. For example, an untagged (i.e., not conjugated to a detectable marker) secondary antibody that selectively binds to an indicator molecule can be bound to a tagged (i.e., conjugated to a detectable marker) tertiary antibody that selectively binds to the secondary antibody. Suitable secondary antibodies, tertiary antibodies and other secondary or tertiary molecules can be selected by those of skill in the art. Preferred secondary molecules of the present invention include an antigen, an anti-IgE idiotypic antibody and an anti-IgE isotypic antibody. Preferred tertiary molecules can be selected by a skilled artisan based upon the characteristics of the secondary molecule. The same strategy is applied for subsequent layers.

In one embodiment, a feline IgE molecule is used as a capture molecule by being immobilized on a substrate, such as a microtiter dish well or a dipstick. A biological sample collected from an animal is applied to the substrate and incubated under conditions suitable to allow for feline IgE molecule:test compound complex formation bound to the substrate. Excess non-bound material, if any, is removed from the substrate under conditions that retain feline IgE molecule:test compound complex binding to the substrate. An indicator molecule that can selectively bind to a test compound bound to the feline IgE molecule is added to the substrate and incubated to allow formation of a complex between the indicator molecule and the feline IgE molecule:test compound complex. Preferably, the indicator molecule is conjugated to a detectable marker (preferably to an enzyme label, to a calorimetric label, to a fluorescent label, to a radioisotope, or to a ligand such as of the biotin or avidin family). Excess indicator molecule is removed, a developing agent is added if required, and the substrate is submitted to a detection device for analysis. Preferred test compounds to detect are FcεR from any animal, antigens or anti-IgE antibodies.

In one embodiment, an immunosorbent assay of the present invention does not utilize a capture molecule. In this embodiment, a test sample is applied to a substrate, such as a microtiter dish well or a dipstick, and incubated under conditions suitable to allow for the test compound binding to the substrate. Any test compound is immobilized on the substrate. Excess non-bound material, if any, is removed from the substrate under conditions that retain test compound binding to the substrate. A feline IgE molecule is added to the substrate and incubated to allow formation of a complex between the feline IgE molecule and the test compound. Preferably, the feline IgE molecule is conjugated to a detectable marker (preferably to biotin, an enzyme label or a fluorescent label). Excess feline IgE molecule is removed, a developing agent is added if required, and the substrate is submitted to a detection device for analysis. Preferred test compounds to detect are Fcε receptor from any animal, antigens or antiIgE antibodies.

Another preferred method to detect a test compound is a lateral flow assay, examples of which are disclosed in U.S. Pat. No. 5,424,193, issued Jun. 13, 1995, by Pronovost et al.; U.S. Pat. No. 5,415,994, issued May 16, 1995, by Imrich et al; WO 94/29696, published Dec. 22, 1994, by Miller et al.; and WO 94/01775, published Jan. 20, 1994, by Pawlak et al.; each of these patent publications is incorporated by reference herein in its entirety. In one embodiment, a biological sample is placed in a lateral flow apparatus that includes the following components: (a) a support structure defining a flow path; (b) a labeling reagent comprising a feline IgE, the labeling reagent being impregnated within the support structure in a labeling zone; and (c) a capture reagent comprising an anti-feline IgE antibody. The capture reagent is located downstream of the labeling reagent within a capture zone fluidly connected to the labeling zone in such a manner that the labeling reagent can flow from the labeling zone into the capture zone. The support structure comprises a material that does not impede the flow of the beads from the labeling zone to the capture zone. Suitable materials for use as a support structure include ionic (i.e., anionic or cationic) material. Examples of such a material include, but are not limited to, nitrocellulose (NC), PVDF, carboxymethylcellulose (CM). The support structure defines a flow path that is lateral and is divided into zones, namely a labeling zone and a capture zone. The apparatus can further comprise a sample receiving zone located along the flow path, more preferably upstream of the labeling reagent. The flow path in the support structure is created by contacting a portion of the support structure downstream of the capture zone, preferably at the end of the flow path, to an absorbent capable of absorbing excess liquid from the labeling and capture zones.

In this embodiment, the biological sample is applied to the sample receiving zone which includes a portion of the support structure. The labeling zone receives the sample from the sample receiving zone which is directed downstream by the flow path. The labeling zone comprises the feline IgE. A preferred labeling reagent is feline IgE conjugated, either directly or through a linker, to a plastic bead substrate, such as to a latex bead. The substrate also includes a detectable marker, preferably a colorimetric marker. Typically, the labeling reagent is impregnated to the support structure by drying or lyophilization. The sample structure also comprises a capture zone downstream of the labeling zone. The capture zone receives labeling reagent from the labeling zone which is directed downstream by the flow path. The capture zone contains the capture reagent, in this case an anti-feline IgE antibody, as disclosed above, that immobilizes the IgE complexed to the anti-IgE in the capture zone. The capture reagent is preferably fixed to the support structure by drying or lyophilizing. The labeling reagent accumulates in the capture zone and the accumulation is assessed visually or by an optical detection device.

Another preferred method is a flow-through assay, examples of which are disclosed in U.S. Pat. No. 4,727,019, issued Feb. 23, 1988, by Valkirs et al, which is incorporated by reference in its entirety.

Also provided by the present invention are methods for inhibiting an immune response to feline IgE, comprising administering a therapeutic composition of the present invention in such a manner so as to reduce feline IgE-mediated immune response.

In another embodiment of the present invention, there are provided methods for eliciting an immune response to feline IgE, comprising administering an immunogen derived from the feline IgE, or a portion thereof. In particular, a method as above, wherein the portion of the IgE molecule is the constant region is preferred. More preferred is a method as above, wherein the portion of the IgE molecule is the Fcε receptor-binding region. Most preferred is a method as above wherein the portion of the IgE molecule is SEQ ID NO 2, SEQ ID NO 4 or SEQ ID NO 6.

The therapeutic compounds and/or compositions can be administered and formulated as described herein.

Also included in the present invention are kits comprising the nucleic acids, proteins or inhibitors of the present invention. In broad terms, a kit may contain feline IgE DNA, antibodies to feline IgE, or feline IgE protein. A kit may be used to detect DNA which hybridizes to feline IgE DNA or to detect the presence of feline IgE protein or peptide fragments in a sample. Such characterization is useful for a variety of purposes including but not limited to forensic analyses and epidemiological studies. Alternatively, a kit may contain DNA molecules, RNA molecules, recombinant protein and antibodies of the present invention for the purpose of screening and measuring levels of feline IgE DNA, feline IgE RNA or feline IgE protein. The recombinant proteins, DNA molecules, RNA molecules and antibodies lend themselves to the formulation of kits suitable for the detection and typing of feline IgE. All of these kits would comprise a compartmentalized carrier suitable to hold in close confinement at least one container. The carrier may also further comprise reagents such as recombinant feline IgE protein or anti-feline IgE antibodies suitable for detecting feline IgE. The carrier may also contain a means for detection such as labeled antigen or enzyme substrates or the like. A preferred kit of the present invention further comprises a detection means including one or more antigens disclosed herein, an antibody capable of selectively binding to an IgE disclosed herein and/or a compound capable of binding to a detectable marker conjugated to a feline IgE protein (e.g., avidin, streptavidin and ImmunoPure® NeutrAvidin when the detectable marker is biotin). Such antigens preferably induce IgE antibody production in animals including canines, felines and/or equines.

In particular, a method and kit of the present invention are useful for diagnosing abnormal conditions in animals that are associated with changing levels of Fcε receptor. Particularly preferred conditions to diagnose include allergies, parasitic infections and neoplasia. For example, a method and kit of the present invention are particularly useful for detecting flea allergy dermatitis (FAD), when such method or kit includes the use of a flea saliva antigen. FAD is defined as a hypersensitive response to fleabites. Preferably, a putative IgE-containing composition is obtained from an animal suspected of having FAD. Preferred animals include those disclosed herein, with dogs and cats being more preferred. In addition, methods and kits of the present invention are particularly useful for detecting helminth infection, in particular heartworm infection, when such methods or kits include the use of a helminth antigen, such as Di33. Preferably, a putative IgE-containing composition is obtained from an animal suspected of having a helminth infection. Preferred animals include those disclosed herein, with dogs and cats being more preferred.

The following examples illustrate the present invention without, however, limiting it. It is to be noted that the Examples include a number of molecular biology, microbiology, immunology and biochemistry techniques considered to be known to those skilled in the art. Disclosure of such techniques can be found, for example, in Sambrook et al., ibid., and related references.

EXAMPLE 1

Isolation of a Nucleic Acid Molecule Encoding a Feline IgE Kappa Light Chain

This example describes the isolation, by DNA hybridization, of a nucleic acid molecule encoding an IgE kappa light chain subunit from *Felis catus*. This nucleic acid molecule was isolated from a feline spleen cDNA library by its ability to hybridize with a $^{32}$P-labelled cDNA encoding the canine IgE kappa light chain subunit.

A feline spleen cDNA library was prepared as follows. Total RNA was extracted from spleen material of a cat using an acid-guanidinium-phenol-chloroform method similar to that described by Chomzynski, et al, 1987, *Anal. Biochem.* 162, 156–159. Poly A$^+$ selected RNA was separated from the total RNA population by oligo-dT cellulose chromatography using the mRNA Purification Kit (available from Pharmacia Biotech, Newark, N.J.), according to the method recommended by the manufacturer. A feline spleen library was constructed in lambda-Uni-ZAP™ XR vector (available from Stratagene, La Jolla, Calif.) using Stratagene's ZAP-cDNA Synthesis Kit protocol. Approximately 5µ g of poly A+ RNA was used to produce the spleen library.

Using a modification of the protocol described in the cDNA Synthesis Kit, the spleen library was screened, using duplicate plaque lifts, with a $^{32}$P-labelled cDNA encoding the canine IgE kappa light chain subunit. Approximately a million plaques were screened under the following conditions. Filters containing plaques were denatured in denaturation buffer consisting of 0.5 N NaOH and 1.5 M NaCl, and neutralized in neutralization buffer consisting of 1.5 M NaCl and 0.5 M Tris-HCl, pH 8.0. Following neutralization, the filters were rinsed briefly in 2×SSC and subjected to UV crosslinking using, for example, a Stratagene UV Stratalinker 1800. The filters were then blocked in hybridization buffer containing 5×SSC, 5× Denhardt's solution, 0.5% SDS, and 100 mg/ml single-stranded DNA for 3 hours at 52° C. The labelled cDNA probe encoding the canine IgE kappa light chain subunit was added, and hybridization was carried out overnight at 52° C. The filters were then washed in 2×SSC, 0.5% SDS at room temperature for 15 minutes, followed by two washes, for 10 minutes each, in 0.2×SSC, 0.1% SDS, at 55° C. The filters were rinsed in 2×SSC, air dried and subjected to autoradiography.

A plaque purified clone of the feline nucleic acid molecule encoding the IgE kappa light chain subunit was converted into a double-stranded DNA molecule using the ExAssist™ helper phage and SOLR™ *E. coli* according to the in vivo excision protocol described in the ZAP-cDNA Synthesis Kit (available from Stratagene). Double-stranded plasmid DNA was prepared using the Quantum Prep Plasmid Midiprep Kit (available from Bio-Rad, Hercules, Calif.), according to the manufacturer's protocol.

The plasmid containing the cDNA encoding the feline IgE kappa light chain was sequenced by the Sanger dideoxy chain termination method, using the PRISM™ Ready Dye Terminator Cycle Sequencing Kit with AmpliTaq DNA Polymerase, FS (available from Perkin Elmer Corporation, Norwalk, Conn.). PCR extensions were done in the Gene-Amp™ Gel Filtration Cartridge (available from Advanced Genetic Technologies, Gaithersburg, Md.) following their standard protocol. Samples were resuspended according to ABI protocols and were run on a Perkin-Elmer ABI-PRISM™ 377 Automated DNA Sequencer. DNA sequence analysis, including the compilation of sequences and the determination of open reading frames, were performed using the MacVector™ program (available from IBI, New Haven, Conn.). Protein sequence analysis, including the determination of molecular weight and isoelectric point (pI) was performed using the GCG™ program (available from Genetics Computer Group, Madison, Wis.).

Sequence analysis indicated that the nucleic acid molecule encoding feline IgE kappa light chain was about 954 nucleotides in length, and, as such, the nucleic acid molecule is referred to herein as nfIgEKLC$_{954}$. Nucleic acid molecule nfIgEKLC$_{954}$ has a coding strand with a nucleic acid sequence of SEQ ID NO: 19 and a complementary strand with a nucleic acid sequence of SEQ ID NO: 21. Translation of SEQ ID NO: 19 indicates that nfIgEKLC$_{954}$ apparently includes a full-length coding region, with the apparent start and stop codons spanning nucleotides 7 through 9 and 733 through 735, respectively, of SEQ ID NO: 19. Putative polyadenylation signals (5' AATAAA 3') are located in a region spanning nucleotides 905 through 910 and nucleotides 909 through 914 of SEQ ID NO: 19. Translation of SEQ ID NO: 19 further indicates that nfIgEKLC$_{954}$ encodes a protein of about 242 amino acids, referred to herein as PfIgEKLC$_{242}$, the amino acid sequence of which is presented in SEQ ID NO: 20. PfIgEKLC$_{242}$ is encoded by nucleic acid molecule nfIgEKLC$_{726}$, which consists of a coding strand having SEQ ID NO: 23 and a complementary strand having SEQ ID NO: 24. SEQ ID NO: 20 predicts a full-length feline IgE kappa light chain protein with an estimated molecular weight of about 26.7 kD and an estimated pI of about 6.5. Analysis of SEQ ID NO: 20 suggests the presence of a signal peptide encoded by a stretch of amino acids spanning from about amino acid 1 through amino acid 20. The proposed mature protein, referred to herein as PfIgEKLC$_{222}$, contains about 222 amino acids which is represented herein as SEQ ID NO: 26, encoded by nucleic acid molecule nfIgEKLC$_{666}$, consisting of a coding strand with a nucleic acid sequence of SEQ ID NO: 25 and a complementary strand with a nucleic acid sequence of SEQ ID NO: 27. SEQ ID NO: 26 predicts a mature feline IgE kappa light chain protein with an estimated molecular weight of about 24.5 kD and an estimated pI of about 6.13.

A BLASTp search was performed by searching the NIH database at The protein search was performed using SEQ ID NO: 20, which showed significant homology to several kappa light chain proteins. The highest scoring match of the homology search at the amino acid level was *Rattus norvegicus* (Norway rat) Ig kappa light chain (AAB03702), which was about 61% identical with SEQ ID NO: 20. At the nucleotide level, the search was performed using SEQ ID NO: 19, which was most similar (sharing 84% nucleotide sequence identity) to the cat kappa light chain sequences (M90809).

EXAMPLE 2

Isolation of a Nucleic Acid Molecule Encoding a Feline IgE Epsilon Heavy Chain

This example describes the isolation, by DNA hybridization, of a nucleic acid molecule encoding an IgE epsilon heavy chain subunit from *Felis catus*. This nucleic acid molecule was isolated from a feline spleen cDNA library in a manner similar to that described in Example 1 except that the labelled probe used was a $^{32}$P-labelled cDNA encoding the canine IgE epsilon heavy chain subunit.

A plaque purified clone of the feline nucleic acid molecule encoding the IgE epsilon heavy chain subunit was converted into a double-stranded plasmid as described in Example 1 and submitted to sequence analysis as described in Example 1.

Sequence analysis indicated that the isolated nucleic acid molecule encoding feline IgE epsilon heavy chain was about 1613 nucleotides, and, as such, the nucleic acid molecule is referred to herein as nfIgEEHC$_{1613}$. Nucleic acid molecule nfIgEEHC$_{1613}$ has a coding strand with a nucleic acid sequence of SEQ ID NO: 1 and a complementary strand with a nucleic acid sequence of SEQ ID NO: 3. Translation of SEQ ID NO: 1 indicates that nfIgEEHC$_{1613}$ apparently includes a partial coding region, with an apparent stop codon spanning nucleotides 1489 through 1491 of SEQ ID NO: 1. A putative polyadenylation signal (5' AATAAA 3') is located in a region spanning nucleotides 1569 through 1574 of SEQ ID NO: 1. Translation of SEQ ID NO: 1 further indicates that nfIgEEHC$_{1613}$ encodes a protein of about 496 amino acids, referred to herein as PfIgEEHC$_{496}$, the amino acid sequence of which is presented in SEQ ID NO: 2. PfIgEEHC$_{496}$ is encoded by nucleic acid molecule nfIgEEHC$_{1488}$, which consists of a coding strand having SEQ ID NO: 31 (with the exception of an g instead of an a at base 205 of SEQ ID NO 31) and a complementary strand having SEQ ID NO: 32 (with an exception of a c instead of a t at the complementary position). SEQ ID NO: 2 predicts a partial feline IgE epsilon heavy chain protein with an estimated molecular weight of about 54.4 kD and an estimated pI of about 6.84 Analysis of SEQ ID NO: 2 suggests that the feline IgE epsilon heavy chain protein includes a partial variable region and an apparent full-length constant region. The amino acid sequence of the partial variable region is denoted by SEQ ID NO: 17 and is encoded by nucleic acid sequence SEQ ID NO: 16, the complement of which is SEQ ID NO: 18. The amino acid sequence of the constant region is denoted by SEQ ID NO: 14 and is encoded by nucleic acid sequence SEQ ID NO: 33 (with noted exception above), the complement of which is SEQ ID NO: 34 (with noted exception above). It is to be noted that SEQ ID NO: 13 also encodes SEQ ID NO: 14, but also contains a 3' untranslated region.

A BLASTp search was performed by searching the NIH database The protein search was performed using SEQ ID NO: 2, which showed significant homology to several IgE epsilon heavy chain proteins. The highest scoring match of the homology search at the amino acid level was canine IgE epsilon heavy chain (Accession number 598109), which was about 76% identical with SEQ ID NO: 2. At the nucleotide level, the search was performed using SEQ ID NO: 1, which was most similar to accession number L36872, canine IgE epsilon heavy chain DNA, the percent identity being 82%.

EXAMPLE 3

Antibodies to Feline IgE Heavy and Light Chains

Feline IgE protein was prepared by passing cat sera through an affinity column of mouse anti-dog IgE monoclonal antibody (mab) produced by the cell line H-47 (available from Custom Mab, West Sacramento, Calif.) bound to Sepharose 4B. Protein retained on the column was eluted with 0.1M Glycine-HCl pH 2.8. The eluted protein was diluted 1:5 with 10 mM Tris-HCl pH 8.0 and applied to a Q-Sepharose column. The column was then eluted sequentially with 0.1M, 0.2M, 0.3M, 0.4M, 0.5M, 0.6M and 1.0M of Tris-HCl pH 8.0 and fractions were collected. The 0.2M and 0.3M fractions were pooled and applied to another affinity column comprising goat anti-cat IgG-Sepharose column (available from Kirkgaard & Perry, Gaithersberg, Md.) bound to Sepharose 4B. The flow-through was collected and found to contain purified cat IgE.

Two Balb/c mice were immunized in the footpad with 30 μg of the purified feline IgE suspended in phosphate buffered saline (PBS) and Freund's complete adjuvant. A boost of 30 μg feline IgE was given in PBS/Freund's incomplete adjuvant in the footpad 14 days after immunization. Sera was tested for presence of anti-feline IgE antibodies 21 days after immunization. The mouse exhibiting the highest titer against feline IgE was boosted with 10 μg antigen in PBS, intravenously 42 days after immunization. Splenocytes were harvested three days later and fused with mouse SP2/0 myeloma cells at mid-log growth phase using PEG.

Cells were cultured in RPMI media containing 20% fetal bovine serum, 10% thymocyte conditioned media, 2 mM L-glutamine, 1 mM sodium pyruvate, 60 μM β-mercaptoethanol and hybrids were selected by adding 100 μM hypoxanthine, 10 μM thymidine and 0.4 μM aminopterin. Wells containing hybridoma colonies were tested for anti-IgE monoclonal antibody production using either feline IgE, IgG and IgM by ELISA using standard techniques.

Eight monoclonal antibodies that bind specifically to feline IgE were generated and are referred to as H-100, H-101, H-102, H-103, H-106, H-99, H-104, and H-107; H-100, H-101, H-102, H-103 and H-106 bind to feline IgE and do not bind to IgG or IgM. These five antibodies also do not react with canine or human IgE. In addition, three monoclonal antibodies reactive to feline IgE light chain were produced and are referred to as H-99, H-104, H-107.

What is claimed is:

1. An isolated protein encoded by a nucleic acid sequence consisting of SEQ ID NO:1, SEQ ID NO 4, SEQ ID NO 7, SEQ ID NO 10, SEQ ID NO 13, SEQ ID NO 16 or SEQ ID NO:28.

2. An isolated protein consisting of an amino acid sequence selected from the group consisting of SEQ ID NO: 2, SEQ ID NO:5, SEQ ID NO:8, SEQ ID NO:11, SEQ ID NO:14, SEQ ID NO:17 and SEQ ID NO:29.

* * * * *

SEQUENCE LISTING

```
<160> NUMBER OF SEQ ID NOS: 34

<210> SEQ ID NO 1
<211> LENGTH: 1613
<212> TYPE: DNA
<213> ORGANISM: Felis catus
<220> FEATURE:
<221> NAME/KEY: CDS
<222> LOCATION: (1)..(1491)

<400> SEQUENCE: 1 gca tat att agt agt gga ggt aac aca gac tac gca gac tcc gtg aag        48
Ala Tyr Ile Ser Ser Gly Gly Asn Thr Asp Tyr Ala Asp Ser Val Lys
 1               5                  10                  15 ggc cga ttc tcc atc tcc aga gac aac gcc aag aac acg ctg tat ctg        96
Gly Arg Phe Ser Ile Ser Arg Asp Asn Ala Lys Asn Thr Leu Tyr Leu
                20                  25                  30 cag atg acc agc ctc aag acc gag gac acg gcc aca tat tac tgt gca       144
Gln Met Thr Ser Leu Lys Thr Glu Asp Thr Ala Thr Tyr Tyr Cys Ala
            35                  40                  45 aga ggg act ggt gta ata ccg gac tac tgg ggc cag gga gcc ctg gtg       192
Arg Gly Thr Gly Val Ile Pro Asp Tyr Trp Gly Gln Gly Ala Leu Val
        50                  55                  60 acg gtg tcc tca gcc tcc atc cag gcc ccc ctc gtc ttc ccc ttg gcc       240
Thr Val Ser Ser Ala Ser Ile Gln Ala Pro Leu Val Phe Pro Leu Ala
 65                  70                  75                  80 acc tgc tgc aaa ggc acc atc gcc act gcc ccg tcc gtg aca ctg ggc       288
Thr Cys Cys Lys Gly Thr Ile Ala Thr Ala Pro Ser Val Thr Leu Gly
                85                  90                  95 tgc ctg gtc acg ggc tac ttc ccg atg ccg gtg act gtg acc tgg gat       336
Cys Leu Val Thr Gly Tyr Phe Pro Met Pro Val Thr Val Thr Trp Asp
            100                 105                 110 gca agg tcc ctg aac aag agc gtc gtg acc ctc ccc gcc acc ctc cag       384
Ala Arg Ser Leu Asn Lys Ser Val Val Thr Leu Pro Ala Thr Leu Gln
        115                 120                 125 gag acc tct ggc ctc tac acc acc agc cac gtg acc gtc tcg ggc           432
Glu Thr Ser Gly Leu Tyr Thr Thr Ser His Val Thr Val Ser Gly
    130                 135                 140 gag tgg gcc aaa cag aag ttc acc tgc agt gtg gct cac gcg gag tcc       480
Glu Trp Ala Lys Gln Lys Phe Thr Cys Ser Val Ala His Ala Glu Ser
145                 150                 155                 160 ccc acc atc aac aag acc gtc agt gcg tgt acc atg aac ttc att ccc       528
Pro Thr Ile Asn Lys Thr Val Ser Ala Cys Thr Met Asn Phe Ile Pro
                165                 170                 175
```

-continued

| | | |
|---|---|---|
| ccc acc gtg aag ctc ttc cac tcc tcc tgt aac ccc ctc ggt gac acc<br>Pro Thr Val Lys Leu Phe His Ser Ser Cys Asn Pro Leu Gly Asp Thr<br>          180                   185               190 | 576 |
| ggt agc acc atc cag ctc ctg tgc ctc atc tcc ggc tac gtc cca ggt<br>Gly Ser Thr Ile Gln Leu Leu Cys Leu Ile Ser Gly Tyr Val Pro Gly<br>        195                  200              205 | 624 |
| gac atg gag gtc acc tgg ctg gtg gat ggg cag aag gcc acg aac ata<br>Asp Met Glu Val Thr Trp Leu Val Asp Gly Gln Lys Ala Thr Asn Ile<br>210                  215                  220 | 672 |
| ttc cca tac act gcc ccc ggc aag cag gag ggc aag gtg acc tcc acc<br>Phe Pro Tyr Thr Ala Pro Gly Lys Gln Glu Gly Lys Val Thr Ser Thr<br>225                  230                  235              240 | 720 |
| cac agc gag ctc aac atc acg cag ggt gag tgg gtg tcc caa aag acc<br>His Ser Glu Leu Asn Ile Thr Gln Gly Glu Trp Val Ser Gln Lys Thr<br>                  245                  250              255 | 768 |
| tac act tgc cag gtc acc tat caa ggc ttc acc ttt gag gac cac gct<br>Tyr Thr Cys Gln Val Thr Tyr Gln Gly Phe Thr Phe Glu Asp His Ala<br>                  260                  265              270 | 816 |
| cgc aag tgc aca gag tct gac ccc cga ggt gtg agc acc tac ttg agc<br>Arg Lys Cys Thr Glu Ser Asp Pro Arg Gly Val Ser Thr Tyr Leu Ser<br>               275                  280              285 | 864 |
| ccg ccc agc cct ctt gac ctg tac gtc cac aag tcg ccc aag atc acc<br>Pro Pro Ser Pro Leu Asp Leu Tyr Val His Lys Ser Pro Lys Ile Thr<br>290                  295                  300 | 912 |
| tgc ctg gtg gtg gac ctg gcc aac aca gac ggc atg atc ctg acc tgg<br>Cys Leu Val Val Asp Leu Ala Asn Thr Asp Gly Met Ile Leu Thr Trp<br>305                  310                  315              320 | 960 |
| tcg cgg gag aat ggg gag tct gtg cac cca gac ccg atg gtc aag aag<br>Ser Arg Glu Asn Gly Glu Ser Val His Pro Asp Pro Met Val Lys Lys<br>                      325                  330              335 | 1008 |
| act cag tac aac ggg aca atc acc gtc act tcc acc ctg cct gtg gat<br>Thr Gln Tyr Asn Gly Thr Ile Thr Val Thr Ser Thr Leu Pro Val Asp<br>                      340                  345              350 | 1056 |
| gcc act gac tgg gtt gag ggg gag acc tac caa tgc aag gtg acc cat<br>Ala Thr Asp Trp Val Glu Gly Glu Thr Tyr Gln Cys Lys Val Thr His<br>               355                  360              365 | 1104 |
| cca gac ctg ccc aag gac atc gtg cgc tcc att gcc aaa gcc ccc ggc<br>Pro Asp Leu Pro Lys Asp Ile Val Arg Ser Ile Ala Lys Ala Pro Gly<br>370                  375                  380 | 1152 |
| cgg cgt ttc ccc ccg gag gtg tac gtg ttc ctg ccg ccc gag ggg gag<br>Arg Arg Phe Pro Pro Glu Val Tyr Val Phe Leu Pro Pro Glu Gly Glu<br>385                  390                  395              400 | 1200 |
| ccg aag acc aag gac aaa gtc att ctc acg tgc ctg atc cag aac ttc<br>Pro Lys Thr Lys Asp Lys Val Ile Leu Thr Cys Leu Ile Gln Asn Phe<br>                      405                  410              415 | 1248 |
| ttt ccc ccg gac atc tcg gtg caa tgg ctt cac aac gac agc cct gtt<br>Phe Pro Pro Asp Ile Ser Val Gln Trp Leu His Asn Asp Ser Pro Val<br>                  420                  425              430 | 1296 |
| cgg aca gaa cag cag gcc acc acg tgg ccc cac aag gcc acc ggc ccc<br>Arg Thr Glu Gln Gln Ala Thr Thr Trp Pro His Lys Ala Thr Gly Pro<br>               435                  440              445 | 1344 |
| agc cca gcc ttc ttt gtc ttc agt cgc ctt gag gtc agc cgg gca gac<br>Ser Pro Ala Phe Phe Val Phe Ser Arg Leu Glu Val Ser Arg Ala Asp<br>450                  455                  460 | 1392 |
| tgg gag cag agg gat gtg ttc acc tgc caa gtg gtg cac gag gcg ctg<br>Trp Glu Gln Arg Asp Val Phe Thr Cys Gln Val Val His Glu Ala Leu<br>465                  470                  475              480 | 1440 |
| cct ggc ttt agg acg ctc aag aaa tcc gtg tcc aaa aac cct ggt aaa<br>Pro Gly Phe Arg Thr Leu Lys Lys Ser Val Ser Lys Asn Pro Gly Lys<br>                      485                  490              495 | 1488 |

-continued

```
tga tgcccacccc tcccccaga gctccatcct gctggggcgg gggaggggcc      1541
ggccggacct gccggtctgt tgttgtcaat aaacactgca gtgcctgcct cagaaaaaaa   1601
aaaaaaaaaa aa                                                      1613
```

<210> SEQ ID NO 2
<211> LENGTH: 496
<212> TYPE: PRT
<213> ORGANISM: Felis catus

<400> SEQUENCE: 2

```
Ala Tyr Ile Ser Ser Gly Gly Asn Thr Asp Tyr Ala Asp Ser Val Lys
 1               5                  10                  15

Gly Arg Phe Ser Ile Ser Arg Asp Asn Ala Lys Asn Thr Leu Tyr Leu
                20                  25                  30

Gln Met Thr Ser Leu Lys Thr Glu Asp Thr Ala Thr Tyr Tyr Cys Ala
            35                  40                  45

Arg Gly Thr Gly Val Ile Pro Asp Tyr Trp Gly Gln Gly Ala Leu Val
        50                  55                  60

Thr Val Ser Ser Ala Ser Ile Gln Ala Pro Leu Val Phe Pro Leu Ala
 65                  70                  75                  80

Thr Cys Cys Lys Gly Thr Ile Ala Thr Ala Pro Ser Val Thr Leu Gly
                 85                  90                  95

Cys Leu Val Thr Gly Tyr Phe Pro Met Pro Val Thr Val Thr Trp Asp
                100                 105                 110

Ala Arg Ser Leu Asn Lys Ser Val Val Thr Leu Pro Ala Thr Leu Gln
            115                 120                 125

Glu Thr Ser Gly Leu Tyr Thr Thr Thr Ser His Val Thr Val Ser Gly
        130                 135                 140

Glu Trp Ala Lys Gln Lys Phe Thr Cys Ser Val Ala His Ala Glu Ser
145                 150                 155                 160

Pro Thr Ile Asn Lys Thr Val Ser Ala Cys Thr Met Asn Phe Ile Pro
                165                 170                 175

Pro Thr Val Lys Leu Phe His Ser Ser Cys Asn Pro Leu Gly Asp Thr
            180                 185                 190

Gly Ser Thr Ile Gln Leu Leu Cys Leu Ile Ser Gly Tyr Val Pro Gly
        195                 200                 205

Asp Met Glu Val Thr Trp Leu Val Asp Gly Gln Lys Ala Thr Asn Ile
    210                 215                 220

Phe Pro Tyr Thr Ala Pro Gly Lys Gln Glu Gly Lys Val Thr Ser Thr
225                 230                 235                 240

His Ser Glu Leu Asn Ile Thr Gln Gly Glu Trp Val Ser Gln Lys Thr
                245                 250                 255

Tyr Thr Cys Gln Val Thr Tyr Gln Gly Phe Thr Phe Glu Asp His Ala
            260                 265                 270

Arg Lys Cys Thr Glu Ser Asp Pro Arg Gly Val Ser Thr Tyr Leu Ser
        275                 280                 285

Pro Pro Ser Pro Leu Asp Leu Tyr Val His Lys Ser Pro Lys Ile Thr
    290                 295                 300

Cys Leu Val Val Asp Leu Ala Asn Thr Asp Gly Met Ile Leu Thr Trp
305                 310                 315                 320

Ser Arg Glu Asn Gly Glu Ser Val His Pro Asp Met Val Lys Lys
                325                 330                 335

Thr Gln Tyr Asn Gly Thr Ile Thr Val Thr Ser Thr Leu Pro Val Asp
            340                 345                 350
```

-continued

```
Ala Thr Asp Trp Val Glu Gly Glu Thr Tyr Gln Cys Lys Val Thr His
        355                 360                 365
Pro Asp Leu Pro Lys Asp Ile Val Arg Ser Ile Ala Lys Ala Pro Gly
    370                 375                 380
Arg Arg Phe Pro Pro Glu Val Tyr Val Phe Leu Pro Pro Glu Gly Glu
385                 390                 395                 400
Pro Lys Thr Lys Asp Lys Val Ile Leu Thr Cys Leu Ile Gln Asn Phe
            405                 410                 415
Phe Pro Pro Asp Ile Ser Val Gln Trp Leu His Asn Asp Ser Pro Val
                420                 425                 430
Arg Thr Glu Gln Gln Ala Thr Thr Trp Pro His Lys Ala Thr Gly Pro
        435                 440                 445
Ser Pro Ala Phe Phe Val Phe Ser Arg Leu Glu Val Ser Arg Ala Asp
    450                 455                 460
Trp Glu Gln Arg Asp Val Phe Thr Cys Gln Val Val His Glu Ala Leu
465                 470                 475                 480
Pro Gly Phe Arg Thr Leu Lys Lys Ser Val Ser Lys Asn Pro Gly Lys
                485                 490                 495
```

<210> SEQ ID NO 3
<211> LENGTH: 1613
<212> TYPE: DNA
<213> ORGANISM: Felis catus

<400> SEQUENCE: 3

| | | | | | |
|---|---|---|---|---|---|
| tttttttttt | tttttttttc | tgaggcaggc | actgcagtgt | ttattgacaa | caacagaccg | 60 |
| gcaggtccgg | ccggcccctc | ccccgcccca | gcaggatgga | gctctggggg | gaggggtggg | 120 |
| catcatttac | cagggttttt | ggacacggat | ttcttgagcg | tcctaaagcc | aggcagcgcc | 180 |
| tcgtgcacca | cttggcaggt | gaacacatcc | ctctgctccc | agtctgcccg | gctgacctca | 240 |
| aggcgactga | agacaaagaa | ggctgggctg | gggccggtgg | ccttgtgggg | ccacgtggtg | 300 |
| gcctgctgtt | ctgtccgaac | agggctgtcg | ttgtgaagcc | attgcaccga | gatgtccggg | 360 |
| ggaaagaagt | tctggatcag | gcacgtgaga | atgactttgt | ccttggtctt | cggctccccc | 420 |
| tcgggcggca | ggaacacgta | cacctccggg | gggaaacgcc | ggccggggc | tttggcaatg | 480 |
| gagcgcacga | tgtccttggg | caggtctgga | tgggtcacct | tgcattggta | ggtctccccc | 540 |
| tcaacccagt | cagtggcatc | acaggcagg | gtggaagtga | cggtgattgt | cccgttgtac | 600 |
| tgagtcttct | tgaccatcgg | gtctgggtgc | acagactccc | cattctcccg | cgaccaggtc | 660 |
| aggatcatgc | cgtctgtgtt | ggccaggtcc | accaccaggc | aggtgatctt | ggcgacttg | 720 |
| tggacgtaca | ggtcaagagg | gctggcgggg | ctcaagtagg | tgctcacacc | tcggggggtca | 780 |
| gactctgtgc | acttgcgagc | gtggtcctca | aggtgaagc | cttgataggt | gacctggcaa | 840 |
| gtgtaggtct | tttgggacac | ccactcaccc | tgcgtgatgt | tgagctcgct | gtgggtggag | 900 |
| gtcaccttgc | cctcctgctt | gccggggggca | gtgtatggga | atatgttcgt | ggccttctgc | 960 |
| ccatccacca | gccaggtgac | ctccatgtca | cctgggacgt | agccggagat | gaggcacagg | 1020 |
| agctggatgg | tgctaccggt | gtcaccgagg | gggttacagg | aggagtggaa | gagcttcacg | 1080 |
| gtggggggaa | tgaagttcat | ggtacacgca | ctgacggtct | tgttgatggt | gggggactcc | 1140 |
| gcgtgagcca | cactgcaggt | gaacttctgt | ttggcccact | cgcccgagac | ggtcacgtgg | 1200 |
| ctggtggtgt | tgtagaggcc | agaggtctcc | tggagggtgg | cggggagggt | cacgacgctc | 1260 |
| ttgttcaggg | accttgcatc | ccaggtcaca | gtcaccggca | tcggaagta | gcccgtgacc | 1320 |

-continued

```
aggcagccca gtgtcacgga cggggcagtg gcgatggtgc ctttgcagca ggtggccaag    1380
gggaagacga ggggggcctg gatggaggct gaggacaccg tcaccagggc tccctggccc    1440
cagtagtccg gtattacacc agtccctctt gcacagtaat atgtggccgt gtcctcggtc    1500
ttgaggctgg tcatctgcag atacagcgtg ttcttggcgt tgtctctgga gatggagaat    1560
cggcccttca cggagtctgc gtagtctgtg ttacctccac tactaatata tgc           1613
```

```
<210> SEQ ID NO 4
<211> LENGTH: 36
<212> TYPE: DNA
<213> ORGANISM: Felis catus
<220> FEATURE:
<221> NAME/KEY: CDS
<222> LOCATION: (1)..(36)

<400> SEQUENCE: 4 agc cct ctt gac ctg tac gtc cac aag tcg ccc aag                      36
Ser Pro Leu Asp Leu Tyr Val His Lys Ser Pro Lys
 1               5                  10
```

```
<210> SEQ ID NO 5
<211> LENGTH: 12
<212> TYPE: PRT
<213> ORGANISM: Felis catus

<400> SEQUENCE: 5

Ser Pro Leu Asp Leu Tyr Val His Lys Ser Pro Lys
 1               5                  10
```

```
<210> SEQ ID NO 6
<211> LENGTH: 36
<212> TYPE: DNA
<213> ORGANISM: Felis catus

<400> SEQUENCE: 6
cttgggcgac ttgtggacgt acaggtcaag agggct                              36
```

```
<210> SEQ ID NO 7
<211> LENGTH: 54
<212> TYPE: DNA
<213> ORGANISM: Felis catus
<220> FEATURE:
<221> NAME/KEY: CDS
<222> LOCATION: (1)..(54)

<400> SEQUENCE: 7 agc ccg ccc agc cct ctt gac ctg tac gtc cac aag tcg ccc aag atc     48
Ser Pro Pro Ser Pro Leu Asp Leu Tyr Val His Lys Ser Pro Lys Ile
 1               5                  10                  15 acc tgc                                                              54
Thr Cys
```

```
<210> SEQ ID NO 8
<211> LENGTH: 18
<212> TYPE: PRT
<213> ORGANISM: Felis catus

<400> SEQUENCE: 8

Ser Pro Pro Ser Pro Leu Asp Leu Tyr Val His Lys Ser Pro Lys Ile
 1               5                  10                  15

Thr Cys
```

```
<210> SEQ ID NO 9
<211> LENGTH: 54
<212> TYPE: DNA
<213> ORGANISM: Felis catus

<400> SEQUENCE: 9
gcaggtgatc ttgggcgact tgtggacgta caggtcaaga gggctgggcg ggct         54

<210> SEQ ID NO 10
<211> LENGTH: 78
<212> TYPE: DNA
<213> ORGANISM: Felis catus
<220> FEATURE:
<221> NAME/KEY: CDS
<222> LOCATION: (1)..(78)

<400> SEQUENCE: 10 agc acc tac ttg agc ccg ccc agc cct ctt gac ctg tac gtc cac aag    48
Ser Thr Tyr Leu Ser Pro Pro Ser Pro Leu Asp Leu Tyr Val His Lys
 1               5                  10                  15 tcg ccc aag atc acc tgc ctg gtg gtg gac                            78
Ser Pro Lys Ile Thr Cys Leu Val Val Asp
            20                  25

<210> SEQ ID NO 11
<211> LENGTH: 26
<212> TYPE: PRT
<213> ORGANISM: Felis catus

<400> SEQUENCE: 11

Ser Thr Tyr Leu Ser Pro Pro Ser Pro Leu Asp Leu Tyr Val His Lys
 1               5                  10                  15

Ser Pro Lys Ile Thr Cys Leu Val Val Asp
            20                  25

<210> SEQ ID NO 12
<211> LENGTH: 78
<212> TYPE: DNA
<213> ORGANISM: Felis catus

<400> SEQUENCE: 12
gtccaccacc aggcaggtga tcttgggcga cttgtggacg tacaggtcaa gagggctggg    60
cgggctcaag taggtgct                                                  78

<210> SEQ ID NO 13
<211> LENGTH: 1418
<212> TYPE: DNA
<213> ORGANISM: Felis catus
<220> FEATURE:
<221> NAME/KEY: CDS
<222> LOCATION: (1)..(1293)

<400> SEQUENCE: 13 gtg tcc tca gcc tcc atc cag gcc ccc ctc gtc ttc ccc ttg gcc acc    48
Val Ser Ser Ala Ser Ile Gln Ala Pro Leu Val Phe Pro Leu Ala Thr
 1               5                  10                  15 tgc tgc aaa ggc acc atc gcc act gcc ccg tcc gtg aca ctg ggc tgc    96
Cys Cys Lys Gly Thr Ile Ala Thr Ala Pro Ser Val Thr Leu Gly Cys
            20                  25                  30 ctg gtc acg ggc tac ttc ccg atg ccg gtg act gtg acc tgg gat gca   144
Leu Val Thr Gly Tyr Phe Pro Met Pro Val Thr Val Thr Trp Asp Ala
        35                  40                  45
```

-continued

| | |
|---|---|
| agg tcc ctg aac aag agc gtc gtg acc ctc ccc gcc acc ctc cag gag<br>Arg Ser Leu Asn Lys Ser Val Val Thr Leu Pro Ala Thr Leu Gln Glu<br>50                      55                    60 | 192 |
| acc tct ggc ctc tac acc acc acc agc cac gtg acc gtc tcg ggc gag<br>Thr Ser Gly Leu Tyr Thr Thr Thr Ser His Val Thr Val Ser Gly Glu<br>65                      70                    75                    80 | 240 |
| tgg gcc aaa cag aag ttc acc tgc agt gtg gct cac gcg gag tcc ccc<br>Trp Ala Lys Gln Lys Phe Thr Cys Ser Val Ala His Ala Glu Ser Pro<br>85                      90                    95 | 288 |
| acc atc aac aag acc gtc agt gcg tgt acc atg aac ttc att ccc ccc<br>Thr Ile Asn Lys Thr Val Ser Ala Cys Thr Met Asn Phe Ile Pro Pro<br>100                    105                  110 | 336 |
| acc gtg aag ctc ttc cac tcc tcc tgt aac ccc ctc ggt gac acc ggt<br>Thr Val Lys Leu Phe His Ser Ser Cys Asn Pro Leu Gly Asp Thr Gly<br>115                    120                  125 | 384 |
| agc acc atc cag ctc ctg tgc ctc atc tcc ggc tac gtc cca ggt gac<br>Ser Thr Ile Gln Leu Leu Cys Leu Ile Ser Gly Tyr Val Pro Gly Asp<br>130                    135                  140 | 432 |
| atg gag gtc acc tgg ctg gtg gat ggg cag aag gcc acg aac ata ttc<br>Met Glu Val Thr Trp Leu Val Asp Gly Gln Lys Ala Thr Asn Ile Phe<br>145                    150                  155                  160 | 480 |
| cca tac act gcc ccc ggc aag cag gag ggc aag gtg acc tcc acc cac<br>Pro Tyr Thr Ala Pro Gly Lys Gln Glu Gly Lys Val Thr Ser Thr His<br>165                    170                  175 | 528 |
| agc gag ctc aac atc acg cag ggt gag tgg gtg tcc caa aag acc tac<br>Ser Glu Leu Asn Ile Thr Gln Gly Glu Trp Val Ser Gln Lys Thr Tyr<br>180                    185                  190 | 576 |
| act tgc cag gtc acc tat caa ggc ttc acc ttt gag gac cac gct cgc<br>Thr Cys Gln Val Thr Tyr Gln Gly Phe Thr Phe Glu Asp His Ala Arg<br>195                    200                  205 | 624 |
| aag tgc aca gag tct gac ccc cga ggt gtg agc acc tac ttg agc ccg<br>Lys Cys Thr Glu Ser Asp Pro Arg Gly Val Ser Thr Tyr Leu Ser Pro<br>210                    215                  220 | 672 |
| ccc agc cct ctt gac ctg tac gtc cac aag tcg ccc aag atc acc tgc<br>Pro Ser Pro Leu Asp Leu Tyr Val His Lys Ser Pro Lys Ile Thr Cys<br>225                    230                  235                  240 | 720 |
| ctg gtg gtg gac ctg gcc aac aca gac ggc atg atc ctg acc tgg tcg<br>Leu Val Val Asp Leu Ala Asn Thr Asp Gly Met Ile Leu Thr Trp Ser<br>245                    250                  255 | 768 |
| cgg gag aat ggg gag tct gtg cac cca gac ccg atg gtc aag aag act<br>Arg Glu Asn Gly Glu Ser Val His Pro Asp Pro Met Val Lys Lys Thr<br>260                    265                  270 | 816 |
| cag tac aac ggg aca atc acc gtc act tcc acc ctg cct gtg gat gcc<br>Gln Tyr Asn Gly Thr Ile Thr Val Thr Ser Thr Leu Pro Val Asp Ala<br>275                    280                  285 | 864 |
| act gac tgg gtt gag ggg gag acc tac caa tgc aag gtg acc cat cca<br>Thr Asp Trp Val Glu Gly Glu Thr Tyr Gln Cys Lys Val Thr His Pro<br>290                    295                  300 | 912 |
| gac ctg ccc aag gac atc gtg cgc tcc att gcc aaa gcc ccc ggc cgg<br>Asp Leu Pro Lys Asp Ile Val Arg Ser Ile Ala Lys Ala Pro Gly Arg<br>305                    310                  315                  320 | 960 |
| cgt ttc ccc ccg gag gtg tac gtg ttc ctg ccg ccc gag ggg gag ccg<br>Arg Phe Pro Pro Glu Val Tyr Val Phe Leu Pro Pro Glu Gly Glu Pro<br>325                    330                  335 | 1008 |
| aag acc aag gac aaa gtc att ctc acg tgc ctg atc cag aac ttc ttt<br>Lys Thr Lys Asp Lys Val Ile Leu Thr Cys Leu Ile Gln Asn Phe Phe<br>340                    345                  350 | 1056 |
| ccc ccg gac atc tcg gtg caa tgg ctt cac aac gac agc cct gtt cgg<br>Pro Pro Asp Ile Ser Val Gln Trp Leu His Asn Asp Ser Pro Val Arg<br>355                    360                  365 | 1104 |

-continued

```
aca gaa cag cag gcc acc acg tgg ccc cac aag gcc acc ggc ccc agc    1152
Thr Glu Gln Gln Ala Thr Thr Trp Pro His Lys Ala Thr Gly Pro Ser
370                 375                 380 cca gcc ttc ttt gtc ttc agt cgc ctt gag gtc agc cgg gca gac tgg    1200
Pro Ala Phe Phe Val Phe Ser Arg Leu Glu Val Ser Arg Ala Asp Trp
385                 390                 395                 400 gag cag agg gat gtg ttc acc tgc caa gtg gtg cac gag gcg ctg cct    1248
Glu Gln Arg Asp Val Phe Thr Cys Gln Val Val His Glu Ala Leu Pro
                405                 410                 415 ggc ttt agg acg ctc aag aaa tcc gtg tcc aaa aac cct ggt aaa        1293
Gly Phe Arg Thr Leu Lys Lys Ser Val Ser Lys Asn Pro Gly Lys
                420                 425                 430 tgatgcccac ccctccccc agagctccat cctgctgggg cggggaggg gccggccgga    1353 cctgccggtc tgttgttgtc aataaacact gcagtgcctg cctcagaaaa aaaaaaaaa   1413 aaaaa                                                               1418
```

<210> SEQ ID NO 14
<211> LENGTH: 431
<212> TYPE: PRT
<213> ORGANISM: Felis catus

<400> SEQUENCE: 14

```
Val Ser Ser Ala Ser Ile Gln Ala Pro Leu Val Phe Pro Leu Ala Thr
1               5                   10                  15

Cys Cys Lys Gly Thr Ile Ala Thr Ala Pro Ser Val Thr Leu Gly Cys
            20                  25                  30

Leu Val Thr Gly Tyr Phe Pro Met Pro Val Thr Val Thr Trp Asp Ala
        35                  40                  45

Arg Ser Leu Asn Lys Ser Val Val Thr Leu Pro Ala Thr Leu Gln Glu
    50                  55                  60

Thr Ser Gly Leu Tyr Thr Thr Thr Ser His Val Thr Val Ser Gly Glu
65                  70                  75                  80

Trp Ala Lys Gln Lys Phe Thr Cys Ser Val Ala His Ala Glu Ser Pro
                85                  90                  95

Thr Ile Asn Lys Thr Val Ser Ala Cys Thr Met Asn Phe Ile Pro Pro
            100                 105                 110

Thr Val Lys Leu Phe His Ser Ser Cys Asn Pro Leu Gly Asp Thr Gly
        115                 120                 125

Ser Thr Ile Gln Leu Leu Cys Leu Ile Ser Gly Tyr Val Pro Gly Asp
    130                 135                 140

Met Glu Val Thr Trp Leu Val Asp Gly Gln Lys Ala Thr Asn Ile Phe
145                 150                 155                 160

Pro Tyr Thr Ala Pro Gly Lys Gln Glu Gly Lys Val Thr Ser Thr His
                165                 170                 175

Ser Glu Leu Asn Ile Thr Gln Gly Glu Trp Val Ser Gln Lys Thr Tyr
            180                 185                 190

Thr Cys Gln Val Thr Tyr Gln Gly Phe Thr Phe Glu Asp His Ala Arg
        195                 200                 205

Lys Cys Thr Glu Ser Asp Pro Arg Gly Val Ser Thr Tyr Leu Ser Pro
    210                 215                 220

Pro Ser Pro Leu Asp Leu Tyr Val His Lys Ser Pro Lys Ile Thr Cys
225                 230                 235                 240

Leu Val Val Asp Leu Ala Asn Thr Asp Gly Met Ile Leu Thr Trp Ser
                245                 250                 255
```

```
Arg Glu Asn Gly Glu Ser Val His Pro Asp Pro Met Val Lys Lys Thr
                260                 265                 270
Gln Tyr Asn Gly Thr Ile Thr Val Thr Ser Thr Leu Pro Val Asp Ala
            275                 280                 285
Thr Asp Trp Val Glu Gly Glu Thr Tyr Gln Cys Lys Val Thr His Pro
        290                 295                 300
Asp Leu Pro Lys Asp Ile Val Arg Ser Ile Ala Lys Ala Pro Gly Arg
305                 310                 315                 320
Arg Phe Pro Pro Glu Val Tyr Val Phe Leu Pro Pro Glu Gly Glu Pro
                325                 330                 335
Lys Thr Lys Asp Lys Val Ile Leu Thr Cys Leu Ile Gln Asn Phe Phe
            340                 345                 350
Pro Pro Asp Ile Ser Val Gln Trp Leu His Asn Asp Ser Pro Val Arg
        355                 360                 365
Thr Glu Gln Gln Ala Thr Thr Trp Pro His Lys Ala Thr Gly Pro Ser
    370                 375                 380
Pro Ala Phe Phe Val Phe Ser Arg Leu Glu Val Ser Arg Ala Asp Trp
385                 390                 395                 400
Glu Gln Arg Asp Val Phe Thr Cys Gln Val Val His Glu Ala Leu Pro
                405                 410                 415
Gly Phe Arg Thr Leu Lys Lys Ser Val Ser Lys Asn Pro Gly Lys
            420                 425                 430
```

<210> SEQ ID NO 15
<211> LENGTH: 1418
<212> TYPE: DNA
<213> ORGANISM: Felis catus

<400> SEQUENCE: 15

```
tttttttttt ttttttttc tgaggcaggc actgcagtgt ttattgacaa caacagaccg      60
gcaggtccgg ccggccccctc ccccgcccca gcaggatgga gctctggggg aggggtggg    120
catcatttac cagggttttt ggacacggat ttcttgagcg tcctaaagcc aggcagcgcc    180
tcgtgcacca cttggcaggt gaacacatcc ctctgctccc agtctgcccg gctgacctca    240
aggcgactga agacaaagaa ggctgggctg gggccggtgg ccttgtgggg ccacgtggtg    300
gcctgctgtt ctgtccgaac agggctgtcg ttgtgaagcc attgcaccga gatgtccggg    360
ggaaagaagt tctggatcag gcacgtgaga atgactttgt ccttggtctt cggctccccc    420
tcgggcggca ggaacacgta cacctccggg ggaaacgcc ggccggggc tttggcaatg     480
gagcgcacga tgtccttggg caggtctgga tgggtcacct gcattggta ggtctccccc     540
tcaacccagt cagtggcatc acaggcaggt ggaagtga cggtgattgt cccgttgtac      600
tgagtcttct tgaccatcgg gtctgggtgc acagactccc cattctcccg cgaccaggtc    660
aggatcatgc cgtctgtgtt ggccaggtcc accaccaggc aggtgatctt gggcgacttg    720
tggacgtaca ggtcaagagg gctgggcggg ctcaagtagg tgctcacacc tcggggtca    780
gactctgtgc acttgcgagc gtggtcctca aggtgaagc cttgataggt gacctggcaa    840
gtgtaggtct tgggacac ccactcaccc tgcgtgatgt tgagctcgct gtgggtggag     900
gtcaccttgc cctcctgctt gccgggggca gtgtatggga atatgttcgt ggccttctgc    960
ccatccacca gccaggtgac ctccatgtca cctgggacgt agccggagat gaggcacagg   1020
agctggatgg tgctaccggt gtcaccgagg gggttacagg aggagtggaa gagcttcacg   1080
gtggggggaa tgaagttcat ggtacacgca ctgacggtct tgttgatggt ggggactcc   1140
```

```
gcgtgagcca cactgcaggt gaacttctgt ttggcccact cgcccgagac ggtcacgtgg    1200
ctggtggtgg tgtagaggcc agaggtctcc tggagggtgg cggggagggt cacgacgctc    1260
ttgttcaggg accttgcatc ccaggtcaca gtcaccggca tcgggaagta gcccgtgacc    1320
aggcagccca gtgtcacgga cggggcagtg gcgatggtgc ctttgcagca ggtggccaag    1380
gggaagacga ggggggcctg gatggaggct gaggacac                            1418
```

<210> SEQ ID NO 16
<211> LENGTH: 195
<212> TYPE: DNA
<213> ORGANISM: Felis catus

<400> SEQUENCE: 16

```
gcatatatta gtagtggagg taacacagac tacgcagact ccgtgaaggg ccgattctcc     60
atctccagag acaacgccaa gaacacgctg tatctgcaga tgaccagcct caagaccgag    120
gacacggcca catattactg tgcaagaggg actggtgtaa taccggacta ctggggccag    180
ggagccctgg tgacg                                                    195
```

<210> SEQ ID NO 17
<211> LENGTH: 64
<212> TYPE: PRT
<213> ORGANISM: Felis catus

<400> SEQUENCE: 17

```
Ala Tyr Ile Ser Ser Gly Gly Asn Thr Asp Tyr Ala Asp Ser Val Lys
 1               5                  10                  15

Gly Arg Phe Ser Ile Ser Arg Asp Asn Ala Lys Asn Thr Leu Tyr Leu
            20                  25                  30

Gln Met Thr Ser Leu Lys Thr Glu Asp Thr Ala Thr Tyr Tyr Cys Ala
        35                  40                  45

Arg Gly Thr Gly Val Ile Pro Asp Tyr Trp Gly Gln Gly Ala Leu Val
    50                  55                  60
```

<210> SEQ ID NO 18
<211> LENGTH: 195
<212> TYPE: DNA
<213> ORGANISM: Felis catus

<400> SEQUENCE: 18

```
cgtcaccagg gctccctggc cccagtagtc cggtattaca ccagtccctc ttgcacagta     60
atatgtggcc gtgtcctcgg tcttgaggct ggtcatctgc agatacagcg tgttcttggc    120
gttgtctctg gagatggaga atcggccctt cacggagtct gcgtagtctg tgttacctcc    180
actactaata tatgc                                                    195
```

<210> SEQ ID NO 19
<211> LENGTH: 954
<212> TYPE: DNA
<213> ORGANISM: Felis catus
<220> FEATURE:
<221> NAME/KEY: CDS
<222> LOCATION: (7)..(732)
<220> FEATURE:

<400> SEQUENCE: 19

```
ctcaaa atg agg ttc cct gct cag ctc ctg gga ctc atc atg ctc tgg       48
       Met Arg Phe Pro Ala Gln Leu Leu Gly Leu Ile Met Leu Trp
        1               5                  10
```

```
atc cca gga tcc agt ggg gat att gtg atg acg cag acc cct ctg tcc        96
Ile Pro Gly Ser Ser Gly Asp Ile Val Met Thr Gln Thr Pro Leu Ser
 15                  20                  25                  30 ctg tcc gtc acc cct gga gag cca gcc tca atc tcc tgc agg gcc agt       144
Leu Ser Val Thr Pro Gly Glu Pro Ala Ser Ile Ser Cys Arg Ala Ser
             35                  40                  45 cag agc ctc ctg tac agt gat gga aat act tat ctg aat tgg tac ctg       192
Gln Ser Leu Leu Tyr Ser Asp Gly Asn Thr Tyr Leu Asn Trp Tyr Leu
         50                  55                  60 cag aag cca ggc cag tct cca cgg cgc ttg atc tat ctt gtt tcc aac       240
Gln Lys Pro Gly Gln Ser Pro Arg Arg Leu Ile Tyr Leu Val Ser Asn
     65                  70                  75 cgg gac tct ggg gtc cca gac agg ttc agt ggc agt ggg tca ggg aca       288
Arg Asp Ser Gly Val Pro Asp Arg Phe Ser Gly Ser Gly Ser Gly Thr
 80                  85                  90 gat ttc acc ctg aga atc agc agg gtg gag gct gac gac gtc ggt gtt       336
Asp Phe Thr Leu Arg Ile Ser Arg Val Glu Ala Asp Asp Val Gly Val
 95                 100                 105                 110 tat tac tgc ggt caa ggt tta cag cat cct ctc act ttc ggc cca ggt       384
Tyr Tyr Cys Gly Gln Gly Leu Gln His Pro Leu Thr Phe Gly Pro Gly
             115                 120                 125 acc aag ctg gag atc aaa cgg agt gat gct cag cca tct gtc ttt ctc       432
Thr Lys Leu Glu Ile Lys Arg Ser Asp Ala Gln Pro Ser Val Phe Leu
         130                 135                 140 ttc caa cca tct ctg gac gag tta cat aca gga agt gcc tct atc gtg       480
Phe Gln Pro Ser Leu Asp Glu Leu His Thr Gly Ser Ala Ser Ile Val
     145                 150                 155 tgc ata ttg aat gac ttc tac ccc aaa gag gtc aat gtc aag tgg aaa       528
Cys Ile Leu Asn Asp Phe Tyr Pro Lys Glu Val Asn Val Lys Trp Lys
 160                 165                 170 gtg gat ggc gta gtc caa aac aaa ggc atc cag gag agc acc aca gag       576
Val Asp Gly Val Val Gln Asn Lys Gly Ile Gln Glu Ser Thr Thr Glu
175                 180                 185                 190 cag aac agc aag gac agc acc tac agc ctc agc agc acc ctg acg atg       624
Gln Asn Ser Lys Asp Ser Thr Tyr Ser Leu Ser Ser Thr Leu Thr Met
             195                 200                 205 tcc agt acg gag tac caa agt cat gaa aag ttc tcc tgc gag gtc act       672
Ser Ser Thr Glu Tyr Gln Ser His Glu Lys Phe Ser Cys Glu Val Thr
         210                 215                 220 cac aag agc ctg gcc tcc acc ctc gtc aag agc ttc aac agg agc gag       720
His Lys Ser Leu Ala Ser Thr Leu Val Lys Ser Phe Asn Arg Ser Glu
     225                 230                 235 tgt cag aga gag tagcctagca ggcctcatca cctgtgcctc agtcccagac           772
Cys Gln Arg Glu
     240 tctctgtctc cctcctcagg cctccggacc tttccccatc ggagacccac acctattgca    832 ggcccttgtc cccaccttac tgcctccccc tctttggctt taatcatgct aataatatat    892 gggggggaaa tgaataaata aagtgaatct ttgcaccagt gaaaaaaaaa aaaaaaaaaa    952 aa                                                                   954

<210> SEQ ID NO 20
<211> LENGTH: 242
<212> TYPE: PRT
<213> ORGANISM: Felis catus
```

<400> SEQUENCE: 20

| | | | | | | | | | | | | | | |
|---|---|---|---|---|---|---|---|---|---|---|---|---|---|---|
|Met|Arg|Phe|Pro|Ala|Gln|Leu|Leu|Gly|Leu|Ile|Met|Leu|Trp|Ile|Pro|
|1| | | |5| | | | |10| | | | |15| |

Gly Ser Ser Gly Asp Ile Val Met Thr Gln Thr Pro Leu Ser Leu Ser
            20                  25                  30

Val Thr Pro Gly Glu Pro Ala Ser Ile Ser Cys Arg Ala Ser Gln Ser
        35                  40                  45

Leu Leu Tyr Ser Asp Gly Asn Thr Tyr Leu Asn Trp Tyr Leu Gln Lys
    50                  55                  60

Pro Gly Gln Ser Pro Arg Arg Leu Ile Tyr Leu Val Ser Asn Arg Asp
65                  70                  75                  80

Ser Gly Val Pro Asp Arg Phe Ser Gly Ser Gly Ser Gly Thr Asp Phe
                85                  90                  95

Thr Leu Arg Ile Ser Arg Val Glu Ala Asp Asp Val Gly Val Tyr Tyr
            100                 105                 110

Cys Gly Gln Gly Leu Gln His Pro Leu Thr Phe Gly Pro Gly Thr Lys
        115                 120                 125

Leu Glu Ile Lys Arg Ser Asp Ala Gln Pro Ser Val Phe Leu Phe Gln
    130                 135                 140

Pro Ser Leu Asp Glu Leu His Thr Gly Ser Ala Ser Ile Val Cys Ile
145                 150                 155                 160

Leu Asn Asp Phe Tyr Pro Lys Glu Val Asn Val Lys Trp Lys Val Asp
                165                 170                 175

Gly Val Val Gln Asn Lys Gly Ile Gln Glu Ser Thr Thr Glu Gln Asn
            180                 185                 190

Ser Lys Asp Ser Thr Tyr Ser Leu Ser Ser Thr Leu Thr Met Ser Ser
        195                 200                 205

Thr Glu Tyr Gln Ser His Glu Lys Phe Ser Cys Glu Val Thr His Lys
    210                 215                 220

Ser Leu Ala Ser Thr Leu Val Lys Ser Phe Asn Arg Ser Glu Cys Gln
225                 230                 235                 240

Arg Glu

<210> SEQ ID NO 21
<211> LENGTH: 954
<212> TYPE: DNA
<213> ORGANISM: Felis catus

<400> SEQUENCE: 21

```
tttttttttt tttttttttt tcactggtgc aaagattcac tttatttatt catttccccc      60
ccatatatta ttagcatgat taaagccaaa gagggggagg cagtaaggtg gggacaaggg     120
cctgcaatag gtgtgggtct ccgatgggga aaggtccgga ggcctgagga gggagacaga     180
gagtctggga ctgaggcaca ggtgatgagg cctgctaggc tactctctct gacactcgct     240
cctgttgaag ctcttgacga gggtggaggc caggctcttg tgagtgacct cgcaggagaa     300
cttttcatga ctttggtact ccgtactgga catcgtcagg gtgctgctga ggctgtaggt     360
gctgtccttg ctgttctgct ctgtggtgct tcctggatg cctttgtttt ggactacgcc     420
atccactttc cacttgacat tgacctcttt ggggtagaag tcattcaata tgcacacgat     480
agaggcactt cctgtatgta actcgtccag agatggttgg aagagaaaga cagatggctg     540
agcatcactc cgtttgatct ccagcttggt acctgggccg aaagtgagag gatgctgtaa     600
accttgaccg cagtaataaa caccgacgtc gtcagcctcc accctgctga ttctcagggt     660
```

```
gaaatctgtc cctgacccac tgccactgaa cctgtctggg accccagagt cccggttgga      720
aacaagatag atcaagcgcc gtggagactg gcctggcttc tgcaggtacc aattcagata      780
agtatttcca tcactgtaca ggaggctctg actggccctg caggagattg aggctggctc      840 tccagggggtg acggacaggg acagagggt ctgcgtcatc acaatatccc cactggatcc      900
tgggatccag agcatgatga gtcccaggag ctgagcaggg aacctcattt tgag            954
```

<210> SEQ ID NO 22
<211> LENGTH: 6
<212> TYPE: DNA
<213> ORGANISM: Felis catus

<400> SEQUENCE: 22

```
aataaa                                                                   6
```

<210> SEQ ID NO 23
<211> LENGTH: 726
<212> TYPE: DNA
<213> ORGANISM: Felis catus

<400> SEQUENCE: 23

```
atgaggttcc ctgctcagct cctgggactc atcatgctct ggatcccagg atccagtggg       60
gatattgtga tgacgcagac ccctctgtcc ctgtccgtca cccctggaga gccagcctca      120
atctcctgca gggccagtca gagcctcctg tacagtgatg aaatactta tctgaattgg       180 tacctgcaga agccaggcca gtctccacgg cgcttgatct atcttgtttc caaccgggac      240
tctggggtcc cagacaggtt cagtggcagt gggtcaggga cagatttcac cctgagaatc      300
agcagggtgg aggctgacga cgtcggtgtt tattactgcg gtcaaggttt acagcatcct      360
ctcactttcg gcccaggtac caagctggag atcaaacgga gtgatgctca gccatctgtc      420
tttctcttcc aaccatctct ggacgagtta catacaggaa gtgcctctat cgtgtgcata      480
ttgaatgact tctaccccaa agaggtcaat gtcaagtgga aagtggatgg cgtagtccaa      540
aacaaaggca tccaggagag caccacagag cagaacagca aggacagcac ctacagcctc      600
agcagcaccc tgacgatgtc cagtacggag taccaaagtc atgaaaagtt ctcctgcgag      660
gtcactcaca agagcctggc ctccacctc gtcaagagct caacaggag cgagtgtcag       720 agagag                                                                 726
```

<210> SEQ ID NO 24
<211> LENGTH: 726
<212> TYPE: DNA
<213> ORGANISM: Felis catus

<400> SEQUENCE: 24

```
ctctctctga cactcgctcc tgttgaagct cttgacgagg gtggaggcca ggctcttgtg       60
agtgacctcg caggagaact tttcatgact ttggtactcc gtactggaca tcgtcagggt      120
gctgctgagg ctgtaggtgc tgtccttgct gttctgctct gtggtgctct cctggatgcc      180
tttgttttgg actacgccat ccactttcca cttgacattg acctctttgg ggtagaagtc      240
attcaatatg cacgcgatag aggcacttcc tgtatgtaac tcgtccagag atggttggaa      300
gagaaagaca gatggctgag catcactccg tttgatctcc agcttggtac ctgggccgaa      360
agtgagagga tgctgtaaac cttgaccgca gtaataaaca ccgacgtcgt cagcctccac      420
cctgctgatt ctcagggtga aatctgtccc tgacccactg ccactgaacc tgtctgggac      480
cccagagtcc cggttggaaa caagatagat caagcgccgt ggagactggc ctggcttctg      540
```

```
caggtaccaa ttcagataag tatttccatc actgtacagg aggctctgac tggccctgca      600
ggagattgag gctggctctc cagggggtgac ggacagggac agagggtct gcgtcatcac      660 aatatcccca ctggatcctg ggatccagag catgatgagt cccaggagct gagcagggaa      720
cctcat                                                                 726

<210> SEQ ID NO 25
<211> LENGTH: 666
<212> TYPE: DNA
<213> ORGANISM: Felis catus

<400> SEQUENCE: 25
gatattgtga tgacgcagac ccctctgtcc ctgtccgtca cccctggaga gccagcctca       60
atctcctgca gggccagtca gagcctcctg tacagtgatg gaaatactta tctgaattgg      120
tacctgcaga agccaggcca gtctccacgg cgcttgatct atcttgtttc caaccgggac      180
tctggggtcc cagacaggtt cagtggcagt gggtcaggga cagatttcac cctgagaatc      240
agcagggtgg aggctgacga cgtcggtgtt tattactgcg gtcaaggttt acagcatcct      300
ctcactttcg gcccaggtac caagctggag atcaaacgga gtgatgctca gccatctgtc      360
tttctcttcc aaccatctct ggacgagtta catacaggaa gtgcctctat cgtgtgcata      420
ttgaatgact tctaccccaa agaggtcaat gtcaagtgga agtggatgg cgtagtccaa      480 aacaaaggca tccaggagag caccacagag cagaacagca aggacagcac ctacagcctc      540
agcagcaccc tgacgatgtc cagtacggag taccaaagtc atgaaaagtt ctcctgcgag      600
gtcactcaca agagcctggc ctccaccctc gtcaagagct caacaggag cgagtgtcag      660 agagag                                                                 666

<210> SEQ ID NO 26
<211> LENGTH: 222
<212> TYPE: PRT
<213> ORGANISM: Felis catus

<400> SEQUENCE: 26

Asp Ile Val Met Thr Gln Thr Pro Leu Ser Leu Ser Val Thr Pro Gly
  1               5                  10                  15

Glu Pro Ala Ser Ile Ser Cys Arg Ala Ser Gln Ser Leu Leu Tyr Ser
             20                  25                  30

Asp Gly Asn Thr Tyr Leu Asn Trp Tyr Leu Gln Lys Pro Gly Gln Ser
         35                  40                  45

Pro Arg Arg Leu Ile Tyr Leu Val Ser Asn Arg Asp Ser Gly Val Pro
     50                  55                  60

Asp Arg Phe Ser Gly Ser Gly Ser Gly Thr Asp Phe Thr Leu Arg Ile
 65                  70                  75                  80

Ser Arg Val Glu Ala Asp Asp Val Gly Val Tyr Tyr Cys Gly Gln Gly
                 85                  90                  95

Leu Gln His Pro Leu Thr Phe Gly Pro Gly Thr Lys Leu Glu Ile Lys
            100                 105                 110

Arg Ser Asp Ala Gln Pro Ser Val Phe Leu Phe Gln Pro Ser Leu Asp
        115                 120                 125

Glu Leu His Thr Gly Ser Ala Ser Ile Val Cys Ile Leu Asn Asp Phe
    130                 135                 140

Tyr Pro Lys Glu Val Asn Val Lys Trp Lys Val Asp Gly Val Val Gln
145                 150                 155                 160
```

```
Asn Lys Gly Ile Gln Glu Ser Thr Thr Glu Gln Asn Ser Lys Asp Ser
            165                 170                 175

Thr Tyr Ser Leu Ser Ser Thr Leu Thr Met Ser Ser Thr Glu Tyr Gln
        180                 185                 190

Ser His Glu Lys Phe Ser Cys Glu Val Thr His Lys Ser Leu Ala Ser
    195                 200                 205

Thr Leu Val Lys Ser Phe Asn Arg Ser Glu Cys Gln Arg Glu
210                 215                 220

<210> SEQ ID NO 27
<211> LENGTH: 666
<212> TYPE: DNA
<213> ORGANISM: Felis catus

<400> SEQUENCE: 27
ctctctctga cactcgctcc tgttgaagct cttgacgagg gtggaggcca ggctcttgtg      60
agtgacctcg caggagaact tttcatgact ttggtactcc gtactggaca tcgtcagggt    120
gctgctgagg ctgtaggtgc tgtccttgct gttctgctct gtggtgctct cctggatgcc    180
tttgttttgg actacgccat ccactttcca cttgacattg acctctttgg ggtagaagtc    240
attcaatatg cacacgatag aggcacttcc tgtatgtaac tcgtccagag atggttggaa    300
gagaaagaca gatggctgag catcactccg tttgatctcc agcttggtac ctgggccgaa    360
agtgagagga tgctgtaaac cttgaccgca gtaataaaca ccgacgtcgt cagcctccac    420
cctgctgatt tcagggtgaa atctgtccc tgacccactg ccactgaacc tgtctgggac     480
cccagagtcc cggttggaaa caagatagat caagcgccgt ggagactggc ctggcttctg    540
caggtaccaa ttcagataag tatttccatc actgtacagg aggctctgac tggccctgca    600
ggagattgag gctggctctc caggggtgac ggacagggac agagggtct gcgtcatcac     660 aatatc                                                                666

<210> SEQ ID NO 28
<211> LENGTH: 1613
<212> TYPE: DNA
<213> ORGANISM: Felis catus

<400> SEQUENCE: 28
gcatatatta gtagtggagg taacacagac tacgcagact ccgtgaaggg ccgattctcc      60
atctccagag acaacgccaa gaacacgctg tatctgcaga tgaccagcct caagaccgag    120
gacacggcca catattactg tgcaagaggg actggtgtaa taccggacta ctggggccag    180
ggagccctgg tgacggtgtc ctcaacctcc atccaggccc cctcgtcttc cccttggcc     240 acctgctgca aaggcaccat cgccactgcc cgtccgtga cactgggctg cctggtcacg    300
ggctacttcc cgatgccggt gactgtgacc tgggatgcaa ggtccctgaa caagagcgtc    360
gtgaccctcc ccgccaccct ccaggagacc tctggcctct acaccaccac cagccacgtg    420
accgtctcgg gcgagtgggc caaacagaag ttcacctgca gtgtggctca cgcggagtcc    480
cccaccatca acaagaccgt cagtgcgtgt accatgaact tcattccccc caccgtgaag    540
ctcttccact cctcctgtaa ccccctcggt gacaccggta gcaccatcca gctcctgtgc    600
ctcatctccg gctacgtccc aggtgacatg gaggtcacct ggctggtgga tgggcagaag    660
gccacgaaca tattcccata cactgccccc ggcaagcagg agggcaaggt gacctccacc    720
cacagcgagc tcaacatcac gcagggtgag tgggtgtccc aaaagaccta cacttgccag    780
gtcacctatc aaggcttcac ctttgaggac cacgctcgca gtgcacaga gtctgacccc    840
```

```
cgaggtgtga gcacctactt gagcccgccc agccctcttg acctgtacgt ccacaagtcg    900
cccaagatca cctgcctggt ggtggacctg ccaacacag acggcatgat cctgacctgg    960
tcgcgggaga atgggagtc tgtgcaccca gacccgatgg tcaagaagac tcagtacaac   1020
gggacaatca ccgtcacttc caccctgcct gtggatgcca ctgactgggt tgaggggag   1080 acctaccaat gcaaggtgac ccatccagac ctgcccaagg acatcgtgcg ctccattgcc   1140 aaagccccg gccggcgttt ccccccggag gtgtacgtgt tcctgccgcc cgaggggag    1200 ccgaagacca aggacaaagt cattctcacg tgcctgatcc agaacttctt cccccggac   1260 atctcggtgc aatggcttca caacgacagc cctgttcgga cagaacagca ggccaccacg   1320
tggccccaca aggccaccgg ccccagccca gccttctttg tcttcagtcg ccttgaggtc   1380
agccgggcag actgggagca gagggatgtg ttcacctgcc aagtggtgca cgaggcgctg   1440
cctggcttta ggacgctcaa gaaatccgtg tccaaaaacc ctggtaaatg atgcccaccc   1500 ctcccccag agctccatcc tgctggggcg ggggaggggc cggccggacc tgccggtctg   1560
ttgttgtcaa taaacactgc agtgcctgcc tcagaaaaaa aaaaaaaaaa aaa          1613
```

<210> SEQ ID NO 29
<211> LENGTH: 496
<212> TYPE: PRT
<213> ORGANISM: Felis catus

<400> SEQUENCE: 29

```
Ala Tyr Ile Ser Ser Gly Gly Asn Thr Asp Tyr Ala Asp Ser Val Lys
 1               5                  10                  15

Gly Arg Phe Ser Ile Ser Arg Asp Asn Ala Lys Asn Thr Leu Tyr Leu
            20                  25                  30

Gln Met Thr Ser Leu Lys Thr Glu Asp Thr Ala Thr Tyr Tyr Cys Ala
        35                  40                  45

Arg Gly Thr Gly Val Ile Pro Asp Tyr Trp Gly Gln Gly Ala Leu Val
    50                  55                  60

Thr Val Ser Ser Thr Ser Ile Gln Ala Pro Leu Val Phe Pro Leu Ala
65                  70                  75                  80

Thr Cys Cys Lys Gly Thr Ile Ala Thr Ala Pro Ser Val Thr Leu Gly
                85                  90                  95

Cys Leu Val Thr Gly Tyr Phe Pro Met Pro Val Thr Val Thr Trp Asp
            100                 105                 110

Ala Arg Ser Leu Asn Lys Ser Val Val Thr Leu Pro Ala Thr Leu Gln
        115                 120                 125

Glu Thr Ser Gly Leu Tyr Thr Thr Thr Ser His Val Thr Val Ser Gly
    130                 135                 140

Glu Trp Ala Lys Gln Lys Phe Thr Cys Ser Val Ala His Ala Glu Ser
145                 150                 155                 160

Pro Thr Ile Asn Lys Thr Val Ser Ala Cys Thr Met Asn Phe Ile Pro
                165                 170                 175

Pro Thr Val Lys Leu Phe His Ser Ser Cys Asn Pro Leu Gly Asp Thr
            180                 185                 190

Gly Ser Thr Ile Gln Leu Leu Cys Leu Ile Ser Gly Tyr Val Pro Gly
        195                 200                 205

Asp Met Glu Val Thr Trp Leu Val Asp Gly Gln Lys Ala Thr Asn Ile
    210                 215                 220

Phe Pro Tyr Thr Ala Pro Gly Lys Gln Glu Gly Lys Val Thr Ser Thr
225                 230                 235                 240
```

-continued

```
His Ser Glu Leu Asn Ile Thr Gln Gly Glu Trp Val Ser Lys Thr
            245                 250                 255
Tyr Thr Cys Gln Val Thr Tyr Gln Gly Phe Thr Phe Glu Asp His Ala
            260                 265                 270
Arg Lys Cys Thr Glu Ser Asp Pro Arg Gly Val Ser Thr Tyr Leu Ser
        275                 280                 285
Pro Pro Ser Pro Leu Asp Leu Tyr Val His Lys Ser Pro Lys Ile Thr
    290                 295                 300
Cys Leu Val Val Asp Leu Ala Asn Thr Asp Gly Met Ile Leu Thr Trp
305                 310                 315                 320
Ser Arg Glu Asn Gly Glu Ser Val His Pro Asp Pro Met Val Lys Lys
                325                 330                 335
Thr Gln Tyr Asn Gly Thr Ile Thr Val Thr Ser Thr Leu Pro Val Asp
            340                 345                 350
Ala Thr Asp Trp Val Glu Gly Glu Thr Tyr Gln Cys Lys Val Thr His
        355                 360                 365
Pro Asp Leu Pro Lys Asp Ile Val Arg Ser Ile Ala Lys Ala Pro Gly
    370                 375                 380
Arg Arg Phe Pro Pro Glu Val Tyr Val Phe Leu Pro Pro Glu Gly Glu
385                 390                 395                 400
Pro Lys Thr Lys Asp Lys Val Ile Leu Thr Cys Leu Ile Gln Asn Phe
                405                 410                 415
Phe Pro Pro Asp Ile Ser Val Gln Trp Leu His Asn Asp Ser Pro Val
            420                 425                 430
Arg Thr Glu Gln Gln Ala Thr Thr Trp Pro His Lys Ala Thr Gly Pro
        435                 440                 445
Ser Pro Ala Phe Phe Val Phe Ser Arg Leu Glu Val Ser Arg Ala Asp
    450                 455                 460
Trp Glu Gln Arg Asp Val Phe Thr Cys Gln Val Val His Glu Ala Leu
465                 470                 475                 480
Pro Gly Phe Arg Thr Leu Lys Lys Ser Val Ser Lys Asn Pro Gly Lys
                485                 490                 495
```

<210> SEQ ID NO 30
<211> LENGTH: 1613
<212> TYPE: DNA
<213> ORGANISM: Felis catus

<400> SEQUENCE: 30

```
ttttttttttt ttttttttttc tgaggcaggc actgcagtgt ttattgacaa caacagaccg      60
gcaggtccgg ccggcccctc ccccgcccca gcaggatgga gctctggggg gaggggtggg     120
catcatttac cagggttttt ggacacggat ttcttgagcg tcctaaagcc aggcagcgcc     180
tcgtgcacca cttggcaggt gaacacatcc ctctgctccc agtctgcccg gctgacctca     240
aggcgactga agacaaagaa ggctgggctg gggccggtgg ccttgtgggg ccacgtggtg     300
gcctgctgtt ctgtccgaac agggctgtcg ttgtgaagcc attgcaccga gatgtccggg     360
ggaaagaagt tctggatcag gcacgtgaga atgactttgt ccttggtctt cggctccccc     420
tcgggcggca ggaacacgta cacctccggg gggaaacgcc ggccggggc tttggcaatg      480
gagcgcacga tgtccttggg cagtctggat gggtcacct gcattggta ggtctccccc       540
tcaacccagt cagtggcatc cacaggcagg gtggaagtga cggtgattgt cccgttgtac     600
tgagtcttct tgaccatcgg gtctgggtgc acagactccc cattctcccg cgaccaggtc     660
aggatcatgc cgtctgtgtt ggccaggtcc accaccaggc aggtgatctt gggcgacttg     720
```

-continued

```
tggacgtaca ggtcaagagg gctgggcggg ctcaagtagg tgctcacacc tcggggtca      780 gactctgtgc acttgcgagc gtggtcctca aggtgaagc cttgataggt gacctggcaa      840
gtgtaggtct tttgggacac ccactcaccc tgcgtgatgt tgagctcgct gtgggtggag     900
gtcaccttgc cctcctgctt gccgggggca gtgtatggga atatgttcgt ggccttctgc     960
ccatccacca gccaggtgac ctccatgtca cctgggacgt agccggagat gaggcacagg    1020
agctggatgg tgctaccggt gtcaccgagg gggttacagg aggagtggaa gagcttcacg    1080 gtgggggga tgaagttcat ggtacacgca ctgacggtct tgttgatggt ggggactcc      1140 gcgtgagcca cactgcaggt gaacttctgt ttggcccact cgcccgagac ggtcacgtgg    1200
ctggtggtgg tgtagaggcc agaggtctcc tggagggtgg cggggagggt cacgacgctc    1260
ttgttcaggg accttgcatc ccaggtcaca gtcaccggca tcgggaagta gcccgtgacc    1320
aggcagccca gtgtcacgga cggggcagtg gcgatggtgc ctttgcagca ggtggccaag    1380
gggaagacga ggggggcctg gatggaggtt gaggacaccg tcaccagggc tccctggccc    1440
cagtagtccg gtattacacc agtccctctt gcacagtaat atgtggccgt gtcctcggtc    1500
ttgaggctgg tcatctgcag atacagcgtg ttcttggcgt tgtctctgga gatggagaat    1560
cggcccttca cggagtctgc gtagtctgtg ttacctccac tactaatata tgc           1613
```

<210> SEQ ID NO 31
<211> LENGTH: 1488
<212> TYPE: DNA
<213> ORGANISM: Felis catus

<400> SEQUENCE: 31

```
gcatatatta gtagtggagg taacacagac tacgcagact ccgtgaaggg ccgattctcc     60
atctccagag acaacgccaa gaacacgctg tatctgcaga tgaccagcct caagaccgag    120
gacacggcca catattactg tgcaagaggg actggtgtaa taccggacta ctggggccag    180
ggagccctgg tgacggtgtc ctcaacctcc atccaggccc ccctcgtctt ccccttggcc    240
acctgctgca aggcaccat cgccactgcc ccgtccgtga cactgggctg cctggtcacg    300
ggctacttcc cgatgccggt gactgtgacc tgggatgcaa ggtccctgaa caagagcgtc    360
gtgaccctcc ccgccaccct ccaggagacc tctggcctct acaccaccac cagccacgtg    420
accgtctcgg gcgagtgggc caaacagaag ttcacctgca gtgtggctca cgcggagtcc    480
cccaccatca acaagaccgt cagtgcgtgt accatgaact tcattccccc caccgtgaag    540
ctcttccact cctcctgtaa cccctcggt gacaccggta gcaccatcca gctcctgtgc    600
ctcatctccg gctacgtccc aggtgacatg gaggtcacct ggctggtgga tgggcagaag    660
gccacgaaca tattcccata cactgccccc ggcaagcagg agggcaaggt gacctccacc    720
cacagcgagc tcaacatcac gcagggtgag tgggtgtccc aaaagaccta cacttgccag    780
gtcacctatc aaggcttcac ctttgaggac cacgctcgca gtgcacaga gtctgacccc    840 cgaggtgtga gcacctactt gagcccgccc agccctcttg acctgtacgt ccacaagtcg    900
cccaagatca ccctgcctgg tggtggacctg gccaacacag acggcatgat cctgacctgg    960
tcgcgggaga atggggagtc tgtgcaccca gacccgatgg tcaagaagac tcagtacaac   1020
gggacaatca ccgtcacttc caccctgcct gtggatgcca ctgactggt tgaggggag     1080 acctaccaat gcaaggtgac ccatccagac ctgcccaagg acatcgtgcg ctccattgcc    1140
aaagcccccg gccggcgttt cccccgag gtgtacgtgt cctgccgcc cgaggggag       1200 ccgaagacca aggacaaagt cattctcacg tgcctgatcc agaacttctt tccccggac     1260
```

| | | | | |
|---|---|---|---|---|
| atctcggtgc | aatggcttca | caacgacagc | cctgttcgga | cagaacagca | ggccaccacg | 1320 |
| tggcccccaca | aggccaccgg | ccccagccca | gccttctttg | tcttcagtcg | ccttgaggtc | 1380 |
| agccgggcag | actgggagca | gagggatgtg | ttcacctgcc | aagtggtgca | cgaggcgctg | 1440 |
| cctggctttta | ggacgctcaa | gaaatccgtg | tccaaaaacc | ctggtaaa | | 1488 |

<210> SEQ ID NO 32
<211> LENGTH: 1488
<212> TYPE: DNA
<213> ORGANISM: Felis catus

<400> SEQUENCE: 32

| | | | | | |
|---|---|---|---|---|---|
| tttaccaggg | tttttggaca | cggatttctt | gagcgtccta | aagccaggca | gcgcctcgtg | 60 |
| caccacttgg | caggtgaaca | catccctctg | ctcccagtct | gcccggctga | cctcaaggcg | 120 |
| actgaagaca | agaaggctg | ggctgggggcc | ggtggccttg | tggggccacg | tggtggcctg | 180 |
| ctgttctgtc | cgaacagggc | tgtcgttgtg | aagccattgc | accagagtgt | ccggggggaaa | 240 |
| gaagttctgg | atcaggcacg | tgagaatgac | tttgtccttg | gtcttcggct | cccccctcggg | 300 |
| cggcaggaac | acgtacacct | ccgggggggaa | acgccggccg | ggggctttgg | caatggagcg | 360 |
| cacgatgtcc | ttgggcaggt | ctggatgggt | caccttgcat | ggtaggtct | ccccctcaac | 420 |
| ccagtcagtg | gcatccacag | gcagggtgga | agtgacggtg | attgtcccgt | tgtactgagt | 480 |
| cttcttgacc | atcgggtctg | ggtgcacaga | ctccccattc | tcccgcgacc | aggtcaggat | 540 |
| catgccgtct | tgttggcca | ggtccaccac | caggcaggtg | atcttgggcg | acttgtggac | 600 |
| gtacaggtca | agagggctgg | gcgggctcaa | gtaggtgctc | acacctcggg | ggtcagactc | 660 |
| tgtgcacttg | cgagcgtggt | cctcaaaggt | gaagccttga | taggtgacct | ggcaagtgta | 720 |
| ggtcttttgg | gacacccact | caccctgcgt | gatgttgagc | tcgctgtggg | tggaggtcac | 780 |
| cttgccctcc | tgcttgccgg | gggcagtgta | tgggaatatg | ttcgtggcct | tctgcccatc | 840 |
| caccagccag | gtgacctcca | tgtcacctgg | gacgtagccg | gagatgaggc | acaggagctg | 900 |
| gatggtgcta | ccggtgtcac | cgaggggggtt | acaggaggag | tggaagagct | tcacggtggg | 960 |
| gggaatgaag | ttcatggtac | acgcactgac | ggtcttgttg | atggtggggg | actccgcgtg | 1020 |
| agccacactg | caggtgaact | tctgtttggc | ccactcgccc | gagacggtca | cgtggctggt | 1080 |
| ggtggtgtag | aggccagagg | tctcctggag | ggtggcgggg | agggtcacga | cgctcttgtt | 1140 |
| cagggaccttt | gcatcccagg | tcacagtcac | cggcatcggg | aagtagcccg | tgaccaggca | 1200 |
| gcccagtgtc | acgacgggg | cagtggcgat | ggtgcctttg | cagcaggtgg | ccaagggggaa | 1260 |
| gacgaggggg | gcctggatgg | aggttgagga | caccgtcacc | agggctccct | ggccccagta | 1320 |
| gtccggtatt | acaccagtcc | ctcttgcaca | gtaaatatgtg | gccgtgtcct | cggtcttgag | 1380 |
| gctggtcatc | tgcagataca | gcgtgttctt | ggcgttgtct | ctggagatgg | agaatcggcc | 1440 |
| cttcacggag | tctgcgtagt | ctgtgttacc | tccactacta | atatatgc | | 1488 |

<210> SEQ ID NO 33
<211> LENGTH: 1293
<212> TYPE: DNA
<213> ORGANISM: Felis catus

<400> SEQUENCE: 33

| | | | | | |
|---|---|---|---|---|---|
| gtgtcctcag | cctccatcca | ggcccccctc | gtcttcccct | tggccacctg | ctgcaaaggc | 60 |
| accatcgcca | ctgccccgtc | cgtgacactg | ggctgcctgg | tcacgggcta | cttcccgatg | 120 |
| ccggtgactg | tgacctggga | tgcaaggtcc | ctgaacaaga | gcgtcgtgac | cctccccgcc | 180 |

| | |
|---|---|
| accctccagg agacctctgg cctctacacc accaccagcc acgtgaccgt ctcgggcgag | 240 |
| tgggccaaac agaagttcac ctgcagtgtg gctcacgcgg agtcccccac catcaacaag | 300 |
| accgtcagtg cgtgtaccat gaacttcatt ccccccaccg tgaagctctt ccactcctcc | 360 |
| tgtaacccc tcggtgacac cggtagcacc atccagctcc tgtgcctcat ctccggctac | 420 |
| gtcccaggtg acatggaggt cacctggctg gtggatgggc agaaggccac gaacatattc | 480 |
| ccatacactg cccccggcaa gcaggagggc aaggtgacct ccacccacag cgagctcaac | 540 |
| atcacgcagg gtgagtgggt gtcccaaaag acctacactt gccaggtcac ctatcaaggc | 600 |
| ttcacctttg aggaccacgc tcgcaagtgc acagagtctg accccgagg tgtgagcacc | 660 |
| tacttgagcc cgcccagccc tcttgacctg tacgtccaca gtcgcccaa gatcacctgc | 720 |
| ctggtggtgg acctggccaa cacagacggc atgatcctga cctggtcgcg ggagaatggg | 780 |
| gagtctgtgc acccagaccc gatggtcaag aagactcagt acaacgggac aatcaccgtc | 840 |
| acttccaccc tgcctgtgga tgccactgac tgggttgagg gggagaccta ccaatgcaag | 900 |
| gtgacccatc cagacctgcc caaggacatc gtgcgctcca ttgccaaagc ccccggccgg | 960 |
| cgtttccccc cggaggtgta cgtgttcctg ccgcccgagg gggagccgaa gaccaaggac | 1020 |
| aaagtcattc tcacgtgcct gatccagaac ttctttcccc cggacatctc ggtgcaatgg | 1080 |
| cttcacaacg acagccctgt tcggacagaa cagcaggcca ccacgtggcc ccacaaggcc | 1140 |
| accggcccca gcccagcctt ctttgtcttc agtcgccttg aggtcagccg gcagactgg | 1200 |
| gagcagaggg atgtgttcac ctgccaagtg gtgcacgagg cgctgcctgg ctttaggacg | 1260 |
| ctcaagaaat ccgtgtccaa aaaccctggt aaa | 1293 |

<210> SEQ ID NO 34
<211> LENGTH: 1293
<212> TYPE: DNA
<213> ORGANISM: Felis catus

<400> SEQUENCE: 34

| | |
|---|---|
| tttaccaggg ttttttggaca cggatttctt gagcgtccta aagccaggca gcgcctcgtg | 60 |
| caccacttgg caggtgaaca catccctctg ctcccagtct gcccggctga cctcaaggcg | 120 |
| actgaagaca aagaaggctg ggctggggcc ggtggccttg tggggccacg tggtggcctg | 180 |
| ctgttctgtc cgaacagggc tgtcgttgtg aagccattgc accgagatgt ccgggggaaa | 240 |
| gaagttctgg atcaggcacg tgagaatgac tttgtccttg gtcttcggct ccccctcggg | 300 |
| cggcaggaac acgtacacct ccgggggga acgccggcc ggggctttgg caatggagcg | 360 |
| cacgatgtcc ttgggcaggt ctggatgggt caccttgcat tggtaggtct cccctcaac | 420 |
| ccagtcagtg gcatccacag gcagggtgga agtgacggtg attgtcccgt tgtactgagt | 480 |
| cttcttgacc atcgggtctg ggtgcacaga ctccccattc tcccgcgacc aggtcaggat | 540 |
| catgccgtct gtgttggcca ggtccaccac caggcaggtg atcttgggcg acttgtggac | 600 |
| gtacaggtca gagggctgg gcgggctcaa gtaggtgctc acctcgggg gtcagactc | 660 |
| tgtgcacttg cgagcgtggt cctcaaaggt gaagccttga taggtgacct ggcaagtgta | 720 |
| ggtcttttgg gacacccact caccctgcgt gatgttgagc tcgctgtggg tggaggtcac | 780 |
| cttgccctcc tgcttgccgg gggcagtgta tgggaatatg ttcgtggcct tctgcccatc | 840 |
| caccagccag gtgacctcca tgtcacctgg gacgtagccg agatgaggc acaggagctg | 900 |
| gatggtgcta ccggtgtcac cgagggggtt acaggaggag tggaagagct tcacggtggg | 960 |
| gggaatgaag ttcatggtac acgcactgac ggtcttgttg atggtggggg actccgcgtg | 1020 |

```
agccacactg caggtgaact tctgtttggc ccactcgccc gagacggtca cgtggctggt    1080
ggtggtgtag aggccagagg tctcctggag ggtggcgggg agggtcacga cgctcttgtt    1140
cagggacctt gcatcccagg tcacagtcac cggcatcggg aagtagcccg tgaccaggca    1200
gcccagtgtc acggacgggg cagtggcgat ggtgcctttg cagcaggtgg ccaaggggaa    1260
gacgaggggg gcctggatgg aggctgagga cac                                 1293
```